US011744964B2

(12) United States Patent
Fraser

(10) Patent No.: US 11,744,964 B2
(45) Date of Patent: Sep. 5, 2023

(54) ELECTRONIC AEROSOL PROVISION SYSTEM AND VAPORIZER THEREFOR

(71) Applicant: NICOVENTURES TRADING LIMITED, London (GB)

(72) Inventor: Rory Fraser, London (GB)

(73) Assignee: Nicoventures Trading Limited, London (GB)

( * ) Notice: Subject to any disclaimer, the term of this patent is extended or adjusted under 35 U.S.C. 154(b) by 310 days.

(21) Appl. No.: 16/096,554

(22) PCT Filed: Apr. 25, 2017

(86) PCT No.: PCT/GB2017/051139

§ 371 (c)(1),
(2) Date: Oct. 25, 2018

(87) PCT Pub. No.: WO2017/187148

PCT Pub. Date: Nov. 2, 2017

(65) Prior Publication Data

US 2019/0133186 A1 May 9, 2019

(30) Foreign Application Priority Data

Apr. 27, 2016 (GB) ..................................... 1607322

(51) Int. Cl.
*A61M 15/06* (2006.01)
*A24F 40/44* (2020.01)
(Continued)

(52) U.S. Cl.
CPC ............. *A61M 15/06* (2013.01); *A24F 40/44* (2020.01); *A24F 40/46* (2020.01); *A24F 40/70* (2020.01);
(Continued)

(58) Field of Classification Search
CPC ............................................ A61M 2016/0018
(Continued)

(56) References Cited

U.S. PATENT DOCUMENTS

| | | | |
|---|---|---|---|
| 228,598 | A | 6/1880 | Buckley |
| 353,327 | A | 11/1886 | Randolph |

(Continued)

FOREIGN PATENT DOCUMENTS

| | | | |
|---|---|---|---|
| AT | 507187 | A4 | 3/2010 |
| AT | 507187 | B1 | 3/2010 |

(Continued)

OTHER PUBLICATIONS

International Preliminary Report on Patentability for corresponding International Application No. PCT/GB2015/051213 dated Jul. 14, 2016.

(Continued)

*Primary Examiner* — Thien S Tran
(74) *Attorney, Agent, or Firm* — Patterson Thuente, P.A.

(57) ABSTRACT

A sub-assembly for an electronic vapor provision system includes a source of liquid for vaporization; and a vaporizer for vaporizing a portion of the liquid for inhalation by a user, the vaporizer including a wick component; and an electrical heating element embedded in the wick component. The wick component includes a sheet of a porous electrically-insulating material and is arranged to wick liquid from the source of liquid to a surface of the wick component adjacent to the embedded electrical heating element for vaporization.

19 Claims, 4 Drawing Sheets

(51) Int. Cl.

| | |
|---|---|
| ***A24F 40/46*** | (2020.01) |
| ***A61M 16/00*** | (2006.01) |
| ***A24F 40/10*** | (2020.01) |
| ***A61M 11/04*** | (2006.01) |
| ***A24F 40/70*** | (2020.01) |

(52) U.S. Cl.

CPC ............ *A61M 11/042* (2014.02); *A24F 40/10* (2020.01); *A61M 2016/0018* (2013.01); *A61M 2205/3653* (2013.01); *A61M 2205/8206* (2013.01)

(58) Field of Classification Search

USPC .......................................................... 392/386

See application file for complete search history.

(56) References Cited

U.S. PATENT DOCUMENTS 576,653 A 2/1897 Bowlby
595,070 A 12/1897 Oldenbusch
744,074 A 11/1903 Hiering
799,844 A 9/1905 Fuller
885,374 A 4/1908 Pohlig
1,163,183 A 12/1915 Stoll
D53,386 S 5/1919 Thomas
1,436,157 A 11/1922 Fazio
1,807,936 A 6/1931 Saunders
1,815,069 A 7/1931 Petro
1,937,120 A 11/1933 Julius et al.
1,937,987 A 12/1933 Sexton
2,057,353 A 10/1936 Whittemore, Jr.
2,262,318 A 11/1941 Fox
2,371,006 A 3/1945 Weaver
2,411,946 A 12/1946 Max et al.
2,467,923 A 4/1949 Allen
2,483,304 A 9/1949 Rudolf et al.
2,522,952 A 9/1950 Joseph
2,658,368 A 11/1953 Siegel
2,782,910 A 2/1957 Saul et al.
2,809,634 A 10/1957 Hirotada
3,080,624 A 3/1963 Weber
3,111,396 A 11/1963 Ball
3,165,225 A 1/1965 Georg et al.
3,221,752 A 12/1965 Strahm
3,402,724 A 9/1968 Blount, et al.
3,431,393 A 3/1969 Katsuda
3,433,632 A 3/1969 Elbert, et al.
3,490,718 A 1/1970 Vary et al.
3,496,336 A 2/1970 Hingorany et al.
3,521,643 A 7/1970 Toth
3,604,428 A 9/1971 Moukaddem
3,722,742 A 3/1973 Wertz
3,743,136 A 7/1973 Chambers
3,804,100 A 4/1974 Fariello
3,861,523 A 1/1975 Fountain et al.
3,863,803 A 2/1975 Valcic
3,964,902 A 6/1976 Fletcher et al.
4,009,713 A 3/1977 Simmons et al.
4,031,906 A 6/1977 Knapp
4,094,119 A 6/1978 Sullivan
4,145,001 A 3/1979 Weyenberg et al.
4,161,283 A 7/1979 Hyman
4,190,412 A 2/1980 Nitta
4,193,513 A 3/1980 Bull
4,214,658 A 7/1980 Crow
4,253,476 A 3/1981 Sato
4,449,039 A * 5/1984 Fukazawa .............. H05B 3/141 219/270
4,503,851 A 3/1985 Braunroth
D279,508 S 7/1985 Shaak et al.
4,588,976 A 5/1986 Jaselli
4,676,237 A 6/1987 Wood et al.
4,677,992 A 7/1987 Bliznak
4,733,794 A 3/1988 Kent
4,735,217 A 4/1988 Gerth et al.
4,753,383 A 6/1988 Focke et al.
4,793,478 A 12/1988 Tudor
4,830,028 A 5/1989 Lawson et al.
4,848,374 A 7/1989 Chard et al.
4,878,832 A 11/1989 Lynch
4,885,129 A 12/1989 Leonard et al.
4,917,301 A 4/1990 Munteanu
4,922,901 A 5/1990 Brooks et al.
4,923,052 A 5/1990 Englebert
4,923,059 A 5/1990 Evers et al.
4,947,874 A 8/1990 Brooks et al.
4,947,875 A 8/1990 Brooks et al.
4,961,438 A 10/1990 Korte
4,978,814 A 12/1990 Honour
5,027,837 A 7/1991 Clearman et al.
5,044,550 A 9/1991 Lamm
5,046,514 A 9/1991 Bolt
5,060,671 A 10/1991 Counts et al.
D322,687 S 12/1991 Tschudin
5,095,647 A 3/1992 Zobele et al.
5,095,921 A 3/1992 Losee et al.
5,096,921 A 3/1992 Bollinger et al.
5,099,861 A 3/1992 Clearman et al.
5,121,881 A 6/1992 Lembeck
5,167,242 A 12/1992 Turner et al.
5,179,966 A 1/1993 Losee et al.
5,247,947 A 9/1993 Clearman
5,269,327 A 12/1993 Counts et al.
D346,878 S 5/1994 Utsch et al.
5,322,075 A 6/1994 Deevi et al.
5,357,271 A 10/1994 Wiklof et al.
5,388,574 A 2/1995 Ingebrethsen
5,390,864 A 2/1995 Alexander
5,404,890 A 4/1995 Gentry et al.
5,408,574 A 4/1995 Deevi et al.
5,448,317 A 9/1995 Huang
5,479,948 A 1/1996 Counts et al.
5,497,792 A 3/1996 Prasad et al.
5,501,236 A 3/1996 Hill et al.
5,505,214 A 4/1996 Collins et al.
5,530,225 A 6/1996 Hajaligol
5,540,241 A 7/1996 Kim
5,553,791 A 9/1996 Alexander
5,568,819 A 10/1996 Gentry et al.
5,636,787 A 6/1997 Gowhari
5,649,554 A 7/1997 Sprinkel et al.
5,659,656 A 8/1997 Das
5,666,977 A 9/1997 Higgins et al.
5,692,291 A 12/1997 Deevi et al.
D392,069 S 3/1998 Rowland
5,743,251 A 4/1998 Howell et al.
D404,201 S 1/1999 Wennerstrom
5,865,185 A 2/1999 Collins et al.
5,875,968 A 3/1999 Miller et al.
5,878,722 A 3/1999 Gras et al.
5,878,752 A 3/1999 Adams et al.
5,896,984 A 4/1999 Focke et al.
D414,892 S 10/1999 Chen
5,967,312 A 10/1999 Jacobs
6,040,560 A 3/2000 Fleischhauer et al.
6,058,711 A 5/2000 Maciaszek et al.
6,065,592 A 5/2000 Wik
6,095,505 A 8/2000 Miller
D432,263 S 10/2000 Issa
D434,217 S 11/2000 Packard et al.
D434,979 S 12/2000 Liu
6,155,268 A 12/2000 Takeuchi
D436,725 S 1/2001 Rogers
D438,003 S 2/2001 Minagawa et al.
D441,133 S 4/2001 Emery
6,275,650 B1 8/2001 Lambert
D449,521 S 10/2001 Pinkus et al.
6,321,757 B1 11/2001 McCutcheon
6,446,793 B1 9/2002 Layshock
D466,012 S 11/2002 Baker
D470,765 S 2/2003 Baker
D471,804 S 3/2003 Staples
D472,012 S 3/2003 South
6,527,166 B1 3/2003 Focke et al.

(56) References Cited

U.S. PATENT DOCUMENTS 6,530,495 B1 3/2003 Joseph
6,561,391 B1 5/2003 Baker
6,652,804 B1 11/2003 Neumann et al.
6,681,998 B2 1/2004 Sharpe et al.
6,701,921 B2 3/2004 Sprinkel, et al.
6,715,605 B1 4/2004 Manservigi et al.
D493,617 S 8/2004 Armato
6,790,496 B1 9/2004 Levander et al.
6,830,046 B2 12/2004 Blakley et al.
D509,732 S 9/2005 Staples
7,100,618 B2 9/2006 Dominguez
7,112,712 B1 9/2006 Ancell
D545,186 S 6/2007 Liebe et al.
D549,573 S 8/2007 Liebe et al.
7,253,282 B2 8/2007 Dehmlow et al.
7,263,228 B2 8/2007 Mori
7,263,282 B2 * 8/2007 Meyer ................. A01M 1/2077
392/386
D550,455 S 9/2007 Barnhart
D566,329 S 4/2008 Bagaric et al.
D566,890 S 4/2008 Bagaric et al.
7,389,878 B1 6/2008 Torrico
D573,889 S 7/2008 Short et al.
7,400,940 B2 7/2008 McRae et al.
D575,451 S 8/2008 Jones et al.
7,455,176 B2 11/2008 Focke, et al.
7,540,286 B2 6/2009 Cross
7,565,969 B2 7/2009 He
D606,854 S 12/2009 Greenhalgh
D610,983 S 3/2010 Wai
D611,806 S 3/2010 Bried
D613,903 S 4/2010 Wu et al.
D613,904 S 4/2010 Wu et al.
D616,753 S 6/2010 Beam et al.
7,767,698 B2 8/2010 Warchol et al.
7,832,410 B2 11/2010 Hon
D628,469 S 12/2010 Taylor et al.
D631,838 S 2/2011 Cheng
D636,257 S 4/2011 Bougoulas et al.
7,992,554 B2 8/2011 Radomski et al.
D649,658 S 11/2011 Belfance et al.
D650,738 S 12/2011 Leung
8,113,343 B2 2/2012 Åkerlind
D656,094 S 3/2012 Wu
8,156,944 B2 4/2012 Han
D661,016 S 5/2012 Borges et al.
D671,677 S 11/2012 Wu
D671,678 S 11/2012 Wu
8,307,834 B1 11/2012 Palmerino, Sr. et al.
D672,642 S 12/2012 Supranowicz
D674,539 S 1/2013 Wu
8,365,742 B2 2/2013 Hon
8,375,957 B2 2/2013 Hon
8,393,331 B2 3/2013 Hon
8,430,106 B2 4/2013 Potter et al.
8,448,783 B2 5/2013 Vecchi
8,490,628 B2 7/2013 Hon
8,511,318 B2 8/2013 Hon
D693,055 S 11/2013 Manca et al.
D700,397 S 2/2014 Manca et al.
8,689,805 B2 4/2014 Hon
8,752,545 B2 6/2014 Buchberger
8,794,245 B1 8/2014 Scatterday
8,833,364 B2 9/2014 Buchberger
D715,760 S 10/2014 Kim et al.
D716,267 S 10/2014 Kim et al.
8,869,793 B1 10/2014 Spandorfer et al.
8,910,640 B2 12/2014 Sears et al.
D720,884 S 1/2015 Liu
8,948,578 B2 2/2015 Buchberger
D723,738 S 3/2015 Liu
8,967,155 B2 3/2015 Bundren et al.
9,055,617 B2 * 6/2015 Thorens ................... H05B 3/58
D736,460 S 8/2015 McKeon et al.
D737,507 S 8/2015 Liu
9,609,894 B2 4/2017 Abramov et al.
9,623,205 B2 4/2017 Buchberger
9,730,276 B2 * 8/2017 Vissa ....................... H05B 3/24
9,943,108 B2 4/2018 Lord
9,961,939 B2 5/2018 Reevell
9,974,335 B2 5/2018 Lord
9,986,760 B2 * 6/2018 Macko .................. A24F 47/008
10,010,695 B2 7/2018 Buchberger
10,045,562 B2 8/2018 Buchberger
10,278,421 B2 5/2019 Lord
10,368,582 B2 8/2019 Lord
2001/0004934 A1 6/2001 Yamamoto et al.
2001/0042546 A1 11/2001 Umeda et al.
2002/0005207 A1 1/2002 Wrenn et al.
2002/0016370 A1 2/2002 Shytle et al.
2002/0079309 A1 6/2002 Cox et al.
2003/0005620 A1 1/2003 Ananth et al.
2003/0049025 A1 3/2003 Neumann et al.
2003/0056791 A1 3/2003 Nichols et al.
2003/0064340 A1 4/2003 Pappas
2003/0079309 A1 5/2003 Vandenbelt et al.
2003/0106552 A1 6/2003 Sprinkel et al.
2003/0108342 A1 6/2003 Sherwood et al.
2003/0108743 A1 6/2003 Anderson
2003/0136399 A1 7/2003 Foley et al.
2003/0136404 A1 7/2003 Hindle et al.
2003/0168057 A1 9/2003 Snyder et al.
2003/0200964 A1 10/2003 Blakley et al.
2003/0202169 A1 10/2003 Liu
2004/0025865 A1 2/2004 Nichols et al.
2004/0031485 A1 2/2004 Rustad et al.
2004/0056651 A1 3/2004 Marietta Bersana
2004/0081624 A1 4/2004 Nguyen et al.
2004/0129793 A1 7/2004 Nguyen et al.
2004/0210151 A1 10/2004 Tsukashima
2004/0223917 A1 11/2004 Hindle et al.
2004/0226568 A1 11/2004 Takeuchi et al.
2004/0255941 A1 12/2004 Nichols et al.
2005/0016550 A1 1/2005 Katase
2005/0063686 A1 3/2005 Whittle et al.
2005/0087460 A1 4/2005 Bruhn et al.
2005/0133049 A1 6/2005 Fournier et al.
2005/0145260 A1 7/2005 Inagaki et al.
2005/0155985 A1 7/2005 Meyer
2005/0194013 A1 9/2005 Wright
2005/0204799 A1 9/2005 Koch
2005/0211243 A1 9/2005 Esser
2005/0224375 A1 10/2005 Focke et al.
2005/0235991 A1 10/2005 Nichols et al.
2005/0268911 A1 12/2005 Cross et al.
2006/0018840 A1 1/2006 Lechuga-Ballesteros et al.
2006/0078477 A1 4/2006 Althouse et al.
2006/0095311 A1 5/2006 Thompson
2006/0137681 A1 6/2006 Von et al.
2006/0180143 A1 8/2006 Lind et al.
2006/0196518 A1 9/2006 Hon
2006/0283468 A1 12/2006 Lipowicz
2007/0014549 A1 1/2007 Demarest et al.
2007/0045288 A1 3/2007 Nelson
2007/0062548 A1 3/2007 Horstmann et al.
2007/0102013 A1 5/2007 Adams et al.
2007/0107879 A1 5/2007 Radomski et al.
2007/0144514 A1 6/2007 Yeates et al.
2007/0155255 A1 7/2007 Galauner et al.
2007/0193895 A1 8/2007 Weiss et al.
2007/0267031 A1 11/2007 Hon
2007/0267032 A1 11/2007 Shan
2008/0017204 A1 1/2008 Braunshteyn et al.
2008/0092912 A1 4/2008 Robinson et al.
2008/0149118 A1 6/2008 Oglesby et al.
2008/0156326 A1 7/2008 Belcastro et al.
2008/0216828 A1 9/2008 Wensley et al.
2008/0223382 A1 9/2008 Zeanah
2008/0241255 A1 10/2008 Rose et al.
2009/0009534 A1 1/2009 Perani et al.
2009/0090472 A1 4/2009 Radomski
2009/0095311 A1 4/2009 Han
2009/0095312 A1 4/2009 Herbrich et al.
2009/0133691 A1 5/2009 Yamada et al.

(56) References Cited

U.S. PATENT DOCUMENTS

| | | | |
|---|---|---|---|
| 2009/0188490 A1 | 7/2009 | Han | |
| 2009/0220222 A1 | 9/2009 | Rabin et al. | |
| 2009/0241947 A1 | 10/2009 | Bedini et al. | |
| 2009/0266837 A1 | 10/2009 | Gelardi et al. | |
| 2009/0272379 A1 | 11/2009 | Thorens et al. | |
| 2009/0288966 A1 | 11/2009 | Minarelli et al. | |
| 2009/0293892 A1 | 12/2009 | Williams et al. | |
| 2009/0324206 A1 | 12/2009 | Young et al. | |
| 2010/0003904 A1 | 1/2010 | Duescher | |
| 2010/0006113 A1 | 1/2010 | Urtsev et al. | |
| 2010/0039066 A1 | 2/2010 | Yuan et al. | |
| 2010/0059070 A1 | 3/2010 | Potter et al. | |
| 2010/0065653 A1 | 3/2010 | Wingo et al. | |
| 2010/0083959 A1 | 4/2010 | Siller | |
| 2010/0108059 A1 | 5/2010 | Axelsson et al. | |
| 2010/0181387 A1 | 7/2010 | Zaffaroni et al. | |
| 2010/0182608 A1 | 7/2010 | Egoyants | |
| 2010/0211011 A1 | 8/2010 | Haar | |
| 2010/0236546 A1 | 9/2010 | Yamada et al. | |
| 2010/0242974 A1 | 9/2010 | Pan | |
| 2010/0313901 A1 | 12/2010 | Fernando et al. | |
| 2011/0011396 A1 | 1/2011 | Fang | |
| 2011/0036363 A1 | 2/2011 | Urtsev et al. | |
| 2011/0094523 A1 | 4/2011 | Thorens et al. | |
| 2011/0126848 A1 | 6/2011 | Zuber | |
| 2011/0155153 A1* | 6/2011 | Thorens | H05B 3/58 131/329 |
| 2011/0155718 A1 | 6/2011 | Greim et al. | |
| 2011/0180433 A1 | 7/2011 | Rennecamp | |
| 2011/0192914 A1 | 8/2011 | Ishigami | |
| 2011/0209717 A1 | 9/2011 | Han | |
| 2011/0226236 A1 | 9/2011 | Buchberger | |
| 2011/0277757 A1 | 11/2011 | Terry | |
| 2011/0278189 A1 | 11/2011 | Terry et al. | |
| 2011/0290267 A1 | 12/2011 | Yamada et al. | |
| 2011/0297166 A1 | 12/2011 | Takeuchi et al. | |
| 2011/0303231 A1 | 12/2011 | Li et al. | |
| 2011/0309157 A1 | 12/2011 | Yang et al. | |
| 2012/0111347 A1 | 5/2012 | Hon | |
| 2012/0145169 A1 | 6/2012 | Wu | |
| 2012/0180994 A1 | 7/2012 | Yang et al. | |
| 2012/0180995 A1 | 7/2012 | Yang et al. | |
| 2012/0199146 A1 | 8/2012 | Marangos | |
| 2012/0227752 A1 | 9/2012 | Alelov | |
| 2012/0227753 A1 | 9/2012 | Newton | |
| 2012/0242974 A1 | 9/2012 | LaValley et al. | |
| 2012/0255567 A1 | 10/2012 | Rose et al. | |
| 2012/0260927 A1 | 10/2012 | Liu | |
| 2012/0285476 A1 | 11/2012 | Hon | |
| 2013/0074857 A1 | 3/2013 | Buchberger | |
| 2013/0081623 A1 | 4/2013 | Buchberger | |
| 2013/0087160 A1 | 4/2013 | Gherghe | |
| 2013/0098786 A1 | 4/2013 | Collins | |
| 2013/0112214 A1 | 5/2013 | Bundren et al. | |
| 2013/0142782 A1 | 6/2013 | Rahmel et al. | |
| 2013/0192615 A1 | 8/2013 | Tucker et al. | |
| 2013/0192619 A1 | 8/2013 | Tucker et al. | |
| 2013/0192621 A1 | 8/2013 | Li et al. | |
| 2013/0192623 A1 | 8/2013 | Tucker et al. | |
| 2013/0213419 A1 | 8/2013 | Tucker et al. | |
| 2013/0228191 A1 | 9/2013 | Newton | |
| 2013/0255702 A1 | 10/2013 | Griffith, Jr. et al. | |
| 2013/0284192 A1 | 10/2013 | Peleg et al. | |
| 2013/0306084 A1 | 11/2013 | Flick | |
| 2013/0319407 A1 | 12/2013 | Liu | |
| 2013/0333700 A1 | 12/2013 | Buchberger | |
| 2013/0340779 A1 | 12/2013 | Liu | |
| 2013/0341218 A1 | 12/2013 | Liu | |
| 2013/0342157 A1 | 12/2013 | Liu | |
| 2014/0000638 A1 | 1/2014 | Sebastian et al. | |
| 2014/0007863 A1 | 1/2014 | Chen | |
| 2014/0007892 A1 | 1/2014 | Liu | |
| 2014/0020697 A1 | 1/2014 | Liu | |
| 2014/0048086 A1 | 2/2014 | Zhanghua | |
| 2014/0053831 A1 | 2/2014 | Leamon et al. | |
| 2014/0060528 A1 | 3/2014 | Liu | |
| 2014/0060554 A1 | 3/2014 | Collett et al. | |
| 2014/0060555 A1 | 3/2014 | Chang et al. | |
| 2014/0064715 A1 | 3/2014 | Greim et al. | |
| 2014/0123989 A1 | 5/2014 | LaMothe | |
| 2014/0182608 A1 | 7/2014 | Egoyants et al. | |
| 2014/0196717 A1 | 7/2014 | Liu | |
| 2014/0196731 A1 | 7/2014 | Scatterday | |
| 2014/0202454 A1 | 7/2014 | Buchberger | |
| 2014/0202476 A1 | 7/2014 | Egoyants et al. | |
| 2014/0209105 A1 | 7/2014 | Sears et al. | |
| 2014/0216485 A1 | 8/2014 | Egoyants et al. | |
| 2014/0238396 A1 | 8/2014 | Buchberger | |
| 2014/0238422 A1 | 8/2014 | Plunkett et al. | |
| 2014/0238423 A1 | 8/2014 | Tucker et al. | |
| 2014/0238424 A1* | 8/2014 | Macko | A24F 47/008 131/328 |
| 2014/0261488 A1 | 9/2014 | Tucker | |
| 2014/0261490 A1 | 9/2014 | Kane | |
| 2014/0261495 A1 | 9/2014 | Novak, III et al. | |
| 2014/0270726 A1 | 9/2014 | Egoyants et al. | |
| 2014/0270730 A1 | 9/2014 | Depiano et al. | |
| 2014/0283825 A1 | 9/2014 | Buchberger | |
| 2014/0286630 A1 | 9/2014 | Buchberger | |
| 2014/0299125 A1 | 10/2014 | Buchberger | |
| 2014/0305431 A1 | 10/2014 | Holley et al. | |
| 2014/0332019 A1 | 11/2014 | Liu | |
| 2014/0338680 A1 | 11/2014 | Abramov et al. | |
| 2015/0114411 A1 | 4/2015 | Buchberger | |
| 2015/0128964 A1 | 5/2015 | Bundren et al. | |
| 2015/0128971 A1 | 5/2015 | Verleur et al. | |
| 2015/0136756 A1* | 5/2015 | Vissa | H05B 3/42 219/541 |
| 2015/0157055 A1 | 6/2015 | Lord | |
| 2015/0164143 A1 | 6/2015 | Maas | |
| 2015/0181934 A1 | 7/2015 | Lyubomirskiy et al. | |
| 2015/0181937 A1 | 7/2015 | Dubief et al. | |
| 2015/0196058 A1 | 7/2015 | Lord | |
| 2015/0201675 A1 | 7/2015 | Lord | |
| 2015/0208728 A1 | 7/2015 | Lord | |
| 2016/0021934 A1 | 1/2016 | Cadieux et al. | |
| 2016/0073693 A1 | 3/2016 | Reevell | |
| 2016/0101909 A1 | 4/2016 | Schennum et al. | |
| 2016/0106154 A1 | 4/2016 | Lord | |
| 2016/0106155 A1 | 4/2016 | Reevell | |
| 2016/0120218 A1 | 5/2016 | Schennum et al. | |
| 2016/0278163 A1 | 9/2016 | Chen | |
| 2016/0353804 A1 | 12/2016 | Lord | |
| 2017/0006916 A1 | 1/2017 | Kimree | |
| 2017/0027225 A1 | 2/2017 | Buchberger et al. | |
| 2017/0042245 A1 | 2/2017 | Buchberger | |
| 2017/0188629 A1 | 7/2017 | Dickens et al. | |
| 2017/0188630 A1 | 7/2017 | Buchberger | |
| 2017/0197043 A1 | 7/2017 | Buchberger | |
| 2017/0197044 A1 | 7/2017 | Buchberger | |
| 2017/0197046 A1 | 7/2017 | Buchberger | |
| 2018/0192705 A1 | 7/2018 | Lord | |
| 2018/0235284 A1 | 8/2018 | Lord | |
| 2019/0254350 A1 | 8/2019 | Lord | |
| 2019/0289920 A1 | 9/2019 | Lord | |

FOREIGN PATENT DOCUMENTS

| | | | |
|---|---|---|---|
| AT | 507188 | A4 | 3/2010 |
| AT | 508244 | | 12/2010 |
| AT | 508244 | A4 | 12/2010 |
| AT | 510405 | A4 | 4/2012 |
| AT | 510504 | A1 | 4/2012 |
| AU | 63931/73 | | 6/1975 |
| AU | 6391373 | A | 6/1975 |
| AU | 6391373 | A | 6/1975 |
| AU | 6393173 | A | 6/1975 |
| AU | 2015359102 | B2 | 6/2018 |
| AU | 2017256084 | B2 | 9/2020 |
| BR | 6402132 | U | 7/1986 |
| CA | 2309376 | | 11/2000 |
| CA | 2309376 | A1 | 11/2000 |
| CA | 2824970 | A1 | 8/2012 |
| CH | 698603 | B1 | 9/2009 |

(56) References Cited

FOREIGN PATENT DOCUMENTS

| | | | |
|---|---|---|---|
| CL | 199400288 | A1 | 8/1995 |
| CL | 199900377 | | 3/1999 |
| CN | 2092880 | | 1/1992 |
| CN | 2092880 | U | 1/1992 |
| CN | 2220168 | | 2/1996 |
| CN | 2220168 | Y | 2/1996 |
| CN | 1126425 | A | 7/1996 |
| CN | 1205849 | A | 1/1999 |
| CN | 1205849 | A | 1/1999 |
| CN | 1312730 | A | 9/2001 |
| CN | 1329567 | A | 1/2002 |
| CN | 1333657 | A | 1/2002 |
| CN | 2485265 | Y | 4/2002 |
| CN | 1530041 | A | 9/2004 |
| CN | 2660914 | Y | 12/2004 |
| CN | 1607911 | A | 4/2005 |
| CN | 2719043 | | 8/2005 |
| CN | 2719043 | Y | 8/2005 |
| CN | 1694765 | A | 11/2005 |
| CN | 1703279 | A | 11/2005 |
| CN | 2754386 | Y | 2/2006 |
| CN | 1286409 | C | 11/2006 |
| CN | 2904674 | Y | 5/2007 |
| CN | 200966824 | Y | 10/2007 |
| CN | 101115901 | A | 1/2008 |
| CN | 201023852 | Y | 2/2008 |
| CN | 201079011 | Y | 7/2008 |
| CN | 20123 8609 | | 5/2009 |
| CN | 201238609 | Y | 5/2009 |
| CN | 201240612 | Y | 5/2009 |
| CN | 201375023 | | 1/2010 |
| CN | 201375023 | Y | 1/2010 |
| CN | 101648041 | A | 2/2010 |
| CN | 101648041 | A | 2/2010 |
| CN | 201430913 | Y | 3/2010 |
| CN | 101843368 | A | 9/2010 |
| CN | 201592850 | U | 9/2010 |
| CN | 101878958 | | 11/2010 |
| CN | 101878958 | A | 11/2010 |
| CN | 101925309 | A | 12/2010 |
| CN | 201657770 | U | 12/2010 |
| CN | 102014677 | A | 4/2011 |
| CN | 201830900 | U | 5/2011 |
| CN | 201860753 | U | 6/2011 |
| CN | 102264249 | A | 11/2011 |
| CN | 102264420 | A | 11/2011 |
| CN | 102326869 | A | 1/2012 |
| CN | 202122096 | U | 1/2012 |
| CN | 102389166 | A | 3/2012 |
| CN | 202172846 | | 3/2012 |
| CN | 202172846 | U | 3/2012 |
| CN | 102655773 | A | 9/2012 |
| CN | 102655773 | A | 9/2012 |
| CN | 102753047 | A | 10/2012 |
| CN | 202722498 | | 2/2013 |
| CN | 202722498 | U | 2/2013 |
| CN | 202750708 | | 2/2013 |
| CN | 202750708 | U | 2/2013 |
| CN | 103052380 | A | 4/2013 |
| CN | 103338664 | A | 10/2013 |
| CN | 103960782 | A | 8/2014 |
| CN | 203986095 | U | 12/2014 |
| CN | 204048047 | U | 12/2014 |
| CN | 104602553 | A | 5/2015 |
| CN | 204317492 | U | 5/2015 |
| CN | 104684422 | A | 6/2015 |
| CN | 204598339 | U | 8/2015 |
| CN | 104983079 | A | 10/2015 |
| CN | 105310114 | A | 2/2016 |
| CN | 105394816 | A | 3/2016 |
| CN | 205106385 | U | 3/2016 |
| CN | 106102863 | A | 11/2016 |
| CN | 106998820 | B | 10/2019 |
| DE | 594585 | | 3/1934 |
| DE | 1950439 | | 4/1971 |
| DE | 1950439 | A1 | 4/1971 |
| DE | 2653133 | A1 | 5/1978 |
| DE | 2940797 | A1 | 4/1981 |
| DE | 3148335 | | 7/1983 |
| DE | 3148335 | A1 | 7/1983 |
| DE | 3218760 | | 12/1983 |
| DE | 3218760 | A1 | 12/1983 |
| DE | 3936687 | A1 | 5/1990 |
| DE | 3936687 | | 5/1992 |
| DE | 29719509 | U1 | 1/1998 |
| DE | 19630619 | | 2/1998 |
| DE | 19630619 | A1 | 2/1998 |
| DE | 19654945 | | 3/1998 |
| DE | 19654945 | A1 | 3/1998 |
| DE | 10330681 | | 6/2004 |
| DE | 10330681 | B3 | 6/2004 |
| DE | 202006013439 | | 10/2006 |
| DE | 202006013439 | U1 | 10/2006 |
| DE | 102006004484 | A1 | 8/2007 |
| DE | 202013100606 | | 2/2013 |
| DE | 202013100606 | U1 | 2/2013 |
| EA | 019736 | B1 | 5/2014 |
| EA | 022685 | B1 | 2/2016 |
| EP | 280262 | | 8/1981 |
| EP | 0280262 | A2 | 8/1988 |
| EP | 0295122 | A2 | 12/1988 |
| EP | 0358002 | A2 | 3/1990 |
| EP | 0358002 | A2 | 3/1990 |
| EP | 0358114 | | 3/1990 |
| EP | 0358114 | A2 | 3/1990 |
| EP | 0444553 | | 9/1991 |
| EP | 0444553 | A2 | 9/1991 |
| EP | 0488488 | A1 | 6/1992 |
| EP | 04888488 | A1 | 6/1992 |
| EP | 0845220 | | 6/1998 |
| EP | 0845220 | A | 6/1998 |
| EP | 0847220 | A2 | 6/1998 |
| EP | 0295122 | | 12/1998 |
| EP | 0893071 | | 1/1999 |
| EP | 0893171 | A1 | 1/1999 |
| EP | 1166814 | A2 | 1/2002 |
| EP | 1166847 | A2 | 1/2002 |
| EP | 1166814 | | 1/2002 |
| EP | 1166847 | | 1/2002 |
| EP | 1468618 | A1 | 10/2004 |
| EP | 1736065 | A1 | 12/2006 |
| EP | 1736065 | | 12/2006 |
| EP | 1757921 | A2 | 2/2007 |
| EP | 1757921 | A2 | 2/2007 |
| EP | 1772166 | A1 | 4/2007 |
| EP | 1772199 | A1 | 4/2007 |
| EP | 1820748 | A1 | 8/2007 |
| EP | 1847671 | A1 | 10/2007 |
| EP | 1950439 | A1 | 7/2008 |
| EP | 2018886 | | 1/2009 |
| EP | 2018886 EP | | 1/2009 |
| EP | 2022349 | | 2/2009 |
| EP | 2022349 | A1 | 2/2009 |
| EP | 2022350 | A1 | 2/2009 |
| EP | 2113178 | | 11/2009 |
| EP | 2113178 | A1 | 11/2009 |
| EP | 2234891 | A2 | 10/2010 |
| EP | 2340729 | A1 | 7/2011 |
| EP | 2358223 | A1 | 8/2011 |
| EP | 2358418 | A1 | 8/2011 |
| EP | 2404515 | A1 | 1/2012 |
| EP | 2468116 | A1 | 6/2012 |
| EP | 2468118 | A1 | 6/2012 |
| EP | 2698070 | | 2/2014 |
| EP | 2698070 | A1 | 2/2014 |
| EP | 2907397 | | 4/2014 |
| EP | 2762019 | | 8/2014 |
| EP | 2762019 | A1 | 8/2014 |
| EP | 2785208 | A1 | 10/2014 |
| EP | 2801273 | A2 | 11/2014 |
| EP | 2835062 | | 2/2015 |
| EP | 2835062 | A1 | 2/2015 |
| EP | 2871985 | A1 | 5/2015 |
| EP | 2907397 | A1 | 8/2015 |

(56) References Cited

FOREIGN PATENT DOCUMENTS

| | | | | |
|---|---|---|---|---|
| EP | 2907397 | B1 | | 9/2017 |
| EP | 3284500 | A1 | | 2/2018 |
| EP | 3117860 | B1 | | 1/2019 |
| EP | 3229621 | B1 | | 1/2020 |
| EP | 3738632 | B1 | | 2/2022 |
| FR | 472030 | A | | 11/1914 |
| FR | 960469 | | | 4/1950 |
| FR | 960469 | A | | 4/1950 |
| FR | 1292446 | A | | 5/1962 |
| GB | 1909/03566 | A | | 6/1909 |
| GB | 190930472 | | | 12/1909 |
| GB | 191100628 | A | | 11/1911 |
| GB | 25575 | | | 3/1912 |
| GB | 191311086 | A | | 9/1913 |
| GB | 110216 | A | | 10/1917 |
| GB | 111454 | A | | 11/1917 |
| GB | 120016 | A | | 10/1918 |
| GB | 160493 | A | | 3/1921 |
| GB | 163124 | A | | 5/1921 |
| GB | 215992 | A | | 5/1924 |
| GB | 220229 | A | | 8/1924 |
| GB | 268967 | A | | 4/1927 |
| GB | 402064 | A | | 11/1933 |
| GB | 438750 | A | | 11/1935 |
| GB | 507955 | A | | 6/1939 |
| GB | 544329 | A | | 4/1942 |
| GB | 565574 | A | | 11/1944 |
| GB | 611596 | A | | 11/1948 |
| GB | 626888 | A | | 7/1949 |
| GB | 871869 | A | | 7/1961 |
| GB | 1313525 | | | 4/1973 |
| GB | 1313525 | A | | 4/1973 |
| GB | 1046183 | | | 7/1988 |
| GB | 2275464 | A | | 8/1994 |
| GB | 2068034 | | | 11/1997 |
| GB | 2369108 | A | | 5/2002 |
| GB | 4000273 | | | 12/2006 |
| GB | 4006615 | | | 10/2008 |
| GB | 2504075 | A | | 1/2014 |
| GB | 2513635 | A | | 11/2014 |
| HK | 1196511 | | | 12/2014 |
| HK | 1196511 | A1 | | 12/2014 |
| HK | 1226611 | | | 10/2017 |
| JP | S5289386 | A | | 7/1977 |
| JP | S57-052456 | | | 3/1982 |
| JP | S5752456 | A | | 3/1982 |
| JP | S57140354 | A | | 8/1982 |
| JP | S59106340 | A | | 6/1984 |
| JP | S59-106340 | | | 1/1986 |
| JP | 61-096765 | | | 5/1986 |
| JP | S61-096763 | | | 5/1986 |
| JP | S6121542 | B2 | | 5/1986 |
| JP | S6196763 | A | | 5/1986 |
| JP | S6196765 | A | | 5/1986 |
| JP | H01117775 | A | | 5/1989 |
| JP | 2124081 | | | 5/1990 |
| JP | H02124081 | A | | 5/1990 |
| JP | H02124082 | A | | 5/1990 |
| JP | H0548944 | A | | 2/1993 |
| JP | H05103836 | A | | 4/1993 |
| JP | H05-309136 | | | 11/1993 |
| JP | H05309136 | A | | 11/1993 |
| JP | 3003543 | U | | 10/1994 |
| JP | H6-315366 | A | | 11/1994 |
| JP | H06303837 | A | | 11/1994 |
| JP | H06315366 | A | | 11/1994 |
| JP | H07147965 | A | | 6/1995 |
| JP | H08-299862 | | | 11/1996 |
| JP | H08299862 | A | | 11/1996 |
| JP | H08511176 | A | | 11/1996 |
| JP | 11089551 | | | 4/1999 |
| JP | H1189551 | A | | 4/1999 |
| JP | H11503912 | A | | 4/1999 |
| JP | H11514018 | A | | 11/1999 |
| JP | H11514018 | A | | 11/1999 |
| JP | H11514081 | A | | 11/1999 |
| JP | 3003543 | B2 | | 1/2000 |
| JP | 2001502542 | A | | 2/2001 |
| JP | 2001248842 | A | | 9/2001 |
| JP | 2002527153 | A | | 8/2002 |
| JP | 3093201 | U | | 4/2003 |
| JP | 2003226577 | A | | 8/2003 |
| JP | 2004097617 | A | | 4/2004 |
| JP | 2004332069 | | | 11/2004 |
| JP | 2004332069 | A | | 11/2004 |
| JP | 2005013092 | A | | 1/2005 |
| JP | 2005034021 | A | | 2/2005 |
| JP | 2005514991 | A | | 5/2005 |
| JP | 2005138773 | A | | 6/2005 |
| JP | 2005524067 | A | | 8/2005 |
| JP | 2005537918 | A | | 12/2005 |
| JP | 2005537918 | A | | 12/2005 |
| JP | 2005537919 | A | | 12/2005 |
| JP | 2005538149 | A | | 12/2005 |
| JP | 2005538159 | A | | 12/2005 |
| JP | 2007057532 | A | | 3/2007 |
| JP | 2007097787 | A | | 4/2007 |
| JP | 2007512880 | A | | 5/2007 |
| JP | 2007297124 | A | | 11/2007 |
| JP | 2008501406 | A | | 1/2008 |
| JP | 2008544834 | A | | 12/2008 |
| JP | 2009509523 | A | | 3/2009 |
| JP | 2009526714 | A | | 7/2009 |
| JP | 2009529871 | A | | 8/2009 |
| JP | 2009537119 | A | | 10/2009 |
| JP | 2010080261 | A | | 4/2010 |
| JP | 2011087569 | A | | 5/2011 |
| JP | 2011515093 | A | | 5/2011 |
| JP | 2011518567 | A | | 6/2011 |
| JP | 2012013247 | A | | 1/2012 |
| JP | 2012026933 | A | | 2/2012 |
| JP | 2012029633 | A | | 2/2012 |
| JP | 2012057859 | A | | 3/2012 |
| JP | 2012506263 | A | | 3/2012 |
| JP | 2012-249854 | | | 12/2012 |
| JP | 2012249854 | A | | 12/2012 |
| JP | 2013516159 | A | | 5/2013 |
| JP | 2013-545473 | A | | 12/2013 |
| JP | 2014501107 | A | | 1/2014 |
| JP | 2014511175 | A | | 5/2014 |
| JP | 2014520542 | A | | 8/2014 |
| JP | 2014524313 | A | | 9/2014 |
| JP | 2014525251 | A | | 9/2014 |
| JP | 2015500025 | A | | 1/2015 |
| JP | 2015505476 | A | | 2/2015 |
| JP | 2015506182 | A | | 3/2015 |
| JP | 2015513970 | A | | 5/2015 |
| JP | 2015521847 | A | | 8/2015 |
| JP | 2017518033 | A | | 7/2017 |
| JP | 2017522868 | A | | 8/2017 |
| JP | 2017525348 | A | | 9/2017 |
| JP | 6507248 | B2 | | 4/2019 |
| KR | 920017172 | A | | 9/1992 |
| KR | 100244670 | B1 | | 2/2000 |
| KR | 20050037919 | A | | 4/2005 |
| KR | 20-2009-0008142 | U | | 8/2009 |
| KR | 20100006995 | U | | 7/2010 |
| KR | 20110006928 | U | | 7/2011 |
| KR | 20120025569 | A | | 3/2012 |
| KR | 20120070731 | A | | 7/2012 |
| KR | 20130004985 | A | | 1/2013 |
| KR | 20130006714 | A | | 1/2013 |
| KR | 2013 0006714 | | | 11/2013 |
| KR | 200470732 | Y1 | * | 1/2014 |
| KR | 20140128449 | A | | 11/2014 |
| KR | 101955000 | B1 | | 3/2019 |
| KR | 102148901 | B1 | | 8/2020 |
| NL | 6617184 | A | | 6/1967 |
| PH | 12017500957 | B1 | | 10/2017 |
| RU | 2311859 | C2 | | 12/2007 |
| RU | 2328192 | C1 | | 7/2008 |
| RU | 2336001 | C2 | | 10/2008 |
| RU | 2360583 | C1 | | 7/2009 |
| RU | 89927 | U1 | | 12/2009 |

(56) References Cited

FOREIGN PATENT DOCUMENTS

| | | | |
|---|---|---|---|
| RU | 89927 | U1 | 12/2009 |
| RU | 94815 | U1 | 6/2010 |
| RU | 94815 | U1 | 6/2010 |
| RU | 103281 | U1 | 4/2011 |
| RU | 103281 | U1 | 4/2011 |
| RU | 115629 | U1 | 5/2012 |
| RU | 115629 | U1 | 5/2012 |
| RU | 121706 | U1 | 11/2012 |
| RU | 122000 | U1 | 11/2012 |
| RU | 122000 | U1 | 11/2012 |
| RU | 124120 | | 1/2013 |
| RU | 124120 | U1 | 1/2013 |
| RU | 132318 | U1 | 9/2013 |
| RU | 2509516 | C2 | 3/2014 |
| UA | 89752 | C2 | 3/2010 |
| UA | 67598 | U | 2/2012 |
| UA | 78167 | U | 3/2013 |
| WO | 9527412 | A1 | 10/1995 |
| WO | WO9527412 | | 10/1995 |
| WO | 9632854 | A2 | 10/1996 |
| WO | WO9632854 | | 10/1996 |
| WO | 9748293 | A1 | 12/1997 |
| WO | WO9748293 | A1 | 12/1997 |
| WO | WO-9817131 | A1 | 4/1998 |
| WO | 0009188 | A1 | 2/2000 |
| WO | WO200009188 | | 2/2000 |
| WO | 0021598 | A1 | 4/2000 |
| WO | WO200021598 | | 4/2000 |
| WO | WO-0028842 | A1 | 5/2000 |
| WO | WO-0050111 | A1 | 8/2000 |
| WO | 01/02040 | A1 | 1/2001 |
| WO | WO-02051468 | A2 | 7/2002 |
| WO | 02058747 | A | 8/2002 |
| WO | WO-02060769 | A1 | 8/2002 |
| WO | WO2002058747 | | 8/2002 |
| WO | WO-03005045 | A1 | 1/2003 |
| WO | 03028409 | A1 | 4/2003 |
| WO | WO2003028409 | A1 | 4/2003 |
| WO | 03050405 | A1 | 6/2003 |
| WO | WO 2003/050405 | A1 | 6/2003 |
| WO | WO-03059424 | A1 | 7/2003 |
| WO | 03083283 | A1 | 10/2003 |
| WO | WO2003083283 | A1 | 10/2003 |
| WO | 03101454 | A1 | 12/2003 |
| WO | WO 2003/101454 | | 12/2003 |
| WO | 2004022128 | A2 | 3/2004 |
| WO | 2004022242 | A1 | 3/2004 |
| WO | 2004022243 | A1 | 3/2004 |
| WO | WO2004/022128 | | 3/2004 |
| WO | WO2004022242 | | 3/2004 |
| WO | WO2004022243 | | 3/2004 |
| WO | 2005106350 | A2 | 11/2005 |
| WO | WO2005106350 | A2 | 11/2005 |
| WO | WO-2005120614 | A1 | 12/2005 |
| WO | 2006082571 | A1 | 8/2006 |
| WO | WO2006082571 | | 8/2006 |
| WO | 2007040941 | A1 | 4/2007 |
| WO | 2007042941 | A2 | 4/2007 |
| WO | WO 2007/042941 | | 4/2007 |
| WO | WO 2007040941 | A2 | 4/2007 |
| WO | WO-2007108877 | A2 | 9/2007 |
| WO | 2007131449 | A1 | 11/2007 |
| WO | WO 2007/131449 | A | 11/2007 |
| WO | WO-2007131448 | A1 | 11/2007 |
| WO | WO-2007141668 | A2 | 12/2007 |
| WO | WO-2008006048 | A2 | 1/2008 |
| WO | WO-2008015918 | A1 | 2/2008 |
| WO | WO-2008038144 | A2 | 4/2008 |
| WO | WO-2008104870 | A1 | 9/2008 |
| WO | WO-2009001085 | A2 | 12/2008 |
| WO | 2009015410 | A1 | 2/2009 |
| WO | WO2009015410 | | 2/2009 |
| WO | WO-2009092862 | A1 | 7/2009 |
| WO | WO-2009092419 | A3 | 9/2009 |
| WO | 2009118085 | A1 | 10/2009 |
| WO | WO2009118085 | A1 | 10/2009 |
| WO | 2009/135729 | A1 | 11/2009 |
| WO | 2009132793 | A1 | 11/2009 |
| WO | WO2009132793 | A1 | 11/2009 |
| WO | 2010045670 | A1 | 4/2010 |
| WO | 2010045671 | A1 | 4/2010 |
| WO | WO2010045670 | A1 | 4/2010 |
| WO | WO2010045671 | A1 | 4/2010 |
| WO | 2011050943 | A1 | 5/2011 |
| WO | WO 2011/050943 | A1 | 5/2011 |
| WO | WO-2011050964 | A1 | 5/2011 |
| WO | WO-2011079932 | A1 | 7/2011 |
| WO | 2011109849 | A1 | 9/2011 |
| WO | WO2011109849 | A1 | 9/2011 |
| WO | WO-2011137453 | A2 | 11/2011 |
| WO | 2012025496 | A1 | 3/2012 |
| WO | WO2012025496 | A1 | 3/2012 |
| WO | WO-2012065310 | A1 | 5/2012 |
| WO | WO-2012065754 | A2 | 5/2012 |
| WO | WO-2012085203 | A1 | 6/2012 |
| WO | WO-2012085207 | A1 | 6/2012 |
| WO | WO-2012106739 | A1 | 8/2012 |
| WO | WO-2012114082 | A1 | 8/2012 |
| WO | WO-2013013808 | A1 | 1/2013 |
| WO | WO-2013025921 | A1 | 2/2013 |
| WO | 2013034453 | A1 | 3/2013 |
| WO | 2013034460 | A1 | 3/2013 |
| WO | WO2013034453 | A1 | 3/2013 |
| WO | WO2013034460 | A1 | 3/2013 |
| WO | 2013057185 | A1 | 4/2013 |
| WO | WO-2013045942 | A2 | 4/2013 |
| WO | WO2013057185 | A1 | 4/2013 |
| WO | 2013082173 | A1 | 6/2013 |
| WO | WO 2013/082173 | | 6/2013 |
| WO | WO-2013083631 | A1 | 6/2013 |
| WO | 2013098395 | A1 | 7/2013 |
| WO | WO2013098395 | A1 | 7/2013 |
| WO | 2013116558 | A1 | 8/2013 |
| WO | WO2013116558 | | 8/2013 |
| WO | WO-2013116571 | A1 | 8/2013 |
| WO | WO-2013116572 | A1 | 8/2013 |
| WO | WO2014130695 | | 8/2013 |
| WO | WO-2013142671 | A1 | 9/2013 |
| WO | 2013152873 | A1 | 10/2013 |
| WO | WO2013152873 | A1 | 10/2013 |
| WO | WO-2013178769 | A1 | 12/2013 |
| WO | WO-2013189050 | A1 | 12/2013 |
| WO | WO-2013189052 | A1 | 12/2013 |
| WO | WO-2014005275 | A1 | 1/2014 |
| WO | WO2014012906 | | 1/2014 |
| WO | WO-2014015463 | A1 | 1/2014 |
| WO | 2014061477 | A1 | 4/2014 |
| WO | WO2014061477 | A1 | 4/2014 |
| WO | WO-2014071329 | A1 | 5/2014 |
| WO | 2014130695 | A1 | 8/2014 |
| WO | 2014140320 | A1 | 9/2014 |
| WO | 2014150131 | A1 | 9/2014 |
| WO | WO2014140320 | A1 | 9/2014 |
| WO | WO2014150131 | A1 | 9/2014 |
| WO | WO-2015114327 | A1 | 8/2015 |
| WO | WO2015114328 | | 8/2015 |
| WO | 2015/149404 | A1 | 10/2015 |
| WO | WO2015165812 | | 11/2015 |
| WO | WO-2015198049 | A1 | 12/2015 |

OTHER PUBLICATIONS

International Search Report for corresponding International Application No. PCT/GB2015/051213 dated Jul. 16, 2015.

Written Opinion of the International Preliminary Examining Authority for International Application No. PCT/GB2015/051213 dated Jul. 16, 2016.

International Search Report and Written Opinion dated Feb. 6, 2013 for PCT/EP0212/070647 filed Oct. 18, 2012.

Chinese Office Action for Chinese Application No. 201480024978.X dated Jan. 18, 2017.

European Search Report for European Application No. 15178588 dated Apr. 14, 2016.

(56) References Cited

OTHER PUBLICATIONS

International Preliminary Report on Patentability, dated Apr. 22, 2014, for International Patent Application No. PCT/EP2012/070647, filed Oct. 18, 2012.
International Search Report and Written Opinion for International Application No. PCT/EP2012/003103, dated Nov. 26, 2012.
International Search Report and Written Opinion for PCT/AT/2012/000017 dated Jul. 3, 2012.
International Search Report and Written Opinion for PCT/GB2014/051333 dated Jul. 17, 2014.
International Search Report and Written Opinion, International Application No. PCT/GB2014/051332 dated Jul. 21, 2014.
International Search Report and Written Opinion, International Application No. PCT/GB2014/051334 dated Jul. 21, 2014.
IPRP dated Aug. 5, 2015 for International Application No. PCT/GB2014/051333.
IPRP, International Application No. PCT/GB2014/051332 dated Nov. 12, 2015.
IPRP, International Application No. PCT/GB2014/051334 dated Nov. 12, 2015.
Japanese Notice of Reasons for Rejection for Japanese Application No. 2015-137361 dated May 31, 2016.
Russian Search Report for Russian Application No. 2015146843/12 (072088) date completed Apr. 24, 2017.
Russian Office Action, Application No. 2014120213/12, dated Oct. 26, 2016, 7 pages.
Russian Office Action, Application No. 2014120213/12, dated Sep. 22, 2017, 11 pages.
Chinese Office Action, Application No. 201480024988.3, dated Dec. 30, 2016, 26 pages.
Chinese Office Action, Application No. 201480024988.3, dated Sep. 11, 2017, 21 pages.
European Extended Search Report, Application No. 17189951.1, dated Jan. 4, 2018, 8 pages (11 pages with translation).
Plasma polymerization (the company Diener electronic GmbH+Co. KG), www.plasma.de, retrieved on Oct. 17, 2017, 19 pages.
International Preliminary Report on Patentability (WIPO English Translation), dated Aug. 13, 2013 for International Patent Application No. PCT/AT2012/000017, filed Feb. 2, 2012.
Pulmonary Pharmacoloy: Delivery Devices and Medications, dated Sep. 6, 2017, 2 pages, available at www.cdeu.org/cecourses/z98207/ch4.htm.
Dunn P and Reay D, Heat Pipes, 4th edition, 1994, ISBN 0080419038, 14 pages.
Application and File History for U.S. Appl. No. 13/125,343, filed Apr. 21, 2011 inventor Buchberger.
Japanese Notice of Reasons for Rejection dated Sep. 8, 2015 for Japanese Application No. 2014179732.
Application and File History for U.S. Appl. No. 14/306,831, filed Jun. 17, 2014, inventor Buchberger.
European Search Report for European Application No. 16166656 dated Oct. 11, 2016.
Notice of Opposition Letter from EPO. Opposition against: EP2358418 dated Mar. 1, 2017.
Rudolph G, Bat Cigarettenfabriken GmbH, 1987, The Influence of CO2 on the Sensory Characteristics of the Favor-System, http://legacy.library.ucsf.edu/tid/sla51f00.
Application and File History for U.S. Appl. No. 15/470,078, filed Mar. 27, 2017, inventor Buchberger.
Application and File History for U.S. Appl. No. 15/470,095, filed Mar. 27, 2017, inventor Buchberger.
Japanese Notification of Reasons for Refusal for Japanese Application No. 2014179732 dated Sep. 3, 2015 dated Sep. 8, 2015.
Japanese Notice of Reasons for Refusal, dated Oct. 7, 2013 dated Oct. 15, 2013 for Japanese Application No. 2011532464.
International Search Report for International Application No. PCT/AT2009/000413 dated Jan. 25, 2010.
Translation of Chinese First Office Action for Chinese Application No. 200980152395.4 dated Dec. 3, 2012.
Translation of Chinese Second Office Action for Chinese Application No. 200980152395.4 dated Aug. 20, 2013.
Japanese Reasons for Rejection for Japanese Application No. 2016134648 dated May 23, 2017.
Japanese Decision to Grant, Application No. 2016-134648, dated May 22, 2018, 3 pages (4 pages with translation).
Japanese Office Action, Application No. 2016-564977, dated Dec. 5, 2017, 3 pages (6 pages with translation).
Japanese Search Report, Application No. 2016-864977, dated Oct. 25, 2017, 9 pages (19 pages with translation).
Chinese Office Action, Application No. 201580022356.8, dated Jul. 18, 2018, 8 pages (15 pages with translation).
International Search Report for International Application No. PCT/AT2009/000414 dated Jan. 26, 2010.
Kynol, *Kynol Standard Specifications of Activated Carbon Fiber Products*, 2 pages, as retrieved on Sep. 19, 2013.
Application and File History for U.S. Appl. No. 14/296,803, filed Jun. 5, 2014 inventor Buchberger.
Application and File History for U.S. Appl. No. 15/454,156, filed Mar. 9, 2017, inventor Buchberger.
Application and File History for U.S. Appl. No. 15/307,095, filed Oct. 27, 2016, inventor Buchberger.
Chinese Office Action, Application No. 2016103 71843.1, dated Sep. 30, 2018, 6 pages (11 pages with translation).
Application and File History for U.S. Appl. No. 15/470,089, filed Mar. 27, 2017, inventor Buchberger.
International Search Report and Written Opinion, Application No. PCT/GB2017/051139, dated Aug. 9, 2017, 16 pages.
International Preliminary Report on Patentability, Application No. PCT/GB2017/051139, dated Aug. 6, 2018, 8 pages.
Application and File History for U.S. Appl. No. 13/984,512, filed Aug. 29, 2013, inventor Buchberger.
Application and File History for U.S. Appl. No. 14/268,909, filed May 2, 2014, inventor Buchberger.
Application and File History for U.S. Appl. No. 15/997,113, filed Jun. 4, 2018, inventor Buchberger.
Application and File History for U.S. Appl. No. 14/353,256, filed Apr. 21, 2014, inventor Buchberger.
Application and File History for U.S. Appl. No. 14/594,065, filed May 12, 2017, inventor Buchberger.
Application and File History for U.S. Appl. No. 14/235,210, filed Mar. 4, 2014, inventor Buchberger.
Application and File History for U.S. Appl. No. 14/787,946, filed Oct. 29, 2015, inventor Lord, 228 pages.
Application and File History for U.S. Appl. No. 14/888,514, filed Nov. 2, 2015, inventor Reevell, 188 pages.
Application and File History for U.S. Appl. No. 14/888,517, filed Nov. 2, 2015, Inventor Reevell, 136 pages.
Company Filtrona Richmond Inc., http://www.filtronaporoustechnologies.com, Nov. 19, 2018, 1 page.
Decision on Appeal, U.S. Appl. No. 14/306,831, dated Mar. 26, 2020, 6 pages.
Decision to Grant dated Feb. 5, 2018 for Ukraine Application No. 201607243, 6 pages.
Decision to Grant dated Apr. 11, 2016 for Russian Application No. 2015100321, 8 pages (No translation available).
Decision to Grant dated Jun. 23, 2016 for Ukrainian Application No. 201500198, 6 pages (No translation available).
Decision to Grant dated Apr. 27, 2017 for Russian Application No. 2015146845, 8 pages.
Decision to Grant for Australian Application No. 2017105898, dated Mar. 16, 2018, 12 pages.
Decision to Grant for Great Britain Application No. GB1405720.2, dated Sep. 26, 2017, 2 pages.
Decision to Grant for Russian Application No. 120267, dated Oct. 26, 2016, 7 pages.
Decision to Grant dated Apr. 1, 2014 for Russian Application No. 2011120430, 16 pages.
Decision to Grant dated Aug. 5, 2014 for Japanese Application No. 2011-532464, 6 pages.
ECF, "Welcome to the World's Largest E-Cigarette Website: The Voice of Vaping since 2007," Nichrome or Kanthal Specs for Purchasing, Apr. 19, 2020, 39 pages.

(56) References Cited

OTHER PUBLICATIONS

Examination Report for Great Britain Application No. GB1405720.2, dated Jun. 27, 2017, 3 pages.
Examination Report dated Nov. 20 for Australian Application No. 2017256084, 3 pages.
Examination Report dated Dec. 15, 2017, for Australian Application No. 201512626, 3 pages.
Extended European Search Report for Application No. 18205608.5, dated Jul. 12, 2019, 7 pages.
Extended European Search Report for Application No. EP17197150.5, dated Mar. 1, 2018, 6 pages.
Extended European Search Report for Application No. 16151458.3, dated Jul. 11, 2016, 8 pages.
Extended European Search Report for Application No. 19196432.9, dated Dec. 9, 2019, 14 pages.
Extended European Search Report for European Application No. 15178588, dated Apr. 22, 2016, 4 pages.
First Office Action for Chinese Application No. 201480031926.5 dated Apr. 21, 2017, 12 pages.
Hegboom T., "Integrating Electrical Heating Elements in Appliance Design," resulting in interlocutory decision dated Aug. 7, 2019, 4 pages.
Hong Kong Publication, Application No. 14110165.2, published on Dec. 19, 2014, 1 page.
Hong Kong Publication, Application No. 16113324.2, published on Oct. 6, 2017, 1 page.
Iatty, "An Idea of the Iatty, Welcome to the World's Largest E-Cigarette Website: The Voice of Vaping since 2007," retrieved on Dec. 17, 2019, p. 23, Post 443, 7 pages.
Iatty, "An Idea of the Iatty, Welcome to the World's Largest E-Cigarette Website: The Voice of Vaping since 2007," retrieved on Dec. 17, 2019, p. 24, Post 467, 6 pages.
Iatty, "An Idea of the Iatty, Welcome to the World's Largest E-Cigarette Website: The Voice of Vaping since 2007," retrieved on Dec. 17, 2019, p. 37, Post 727, 6 pages.
Iatty, "An Idea of the Iatty, Welcome to the World's Largest E-Cigarette Website: The Voice of Vaping since 2007," retrieved on Dec. 17, 2019, Page, Post 1, 7 pages.
Iatty, "E-Cigarette Forum," Imeothansis and Iorderos33, p. 10, Feb. 11, 2019, 8 pages.
"Integrating Electrical Heating Elements in Product Design," Metallic Resistance Heating Wire, Chapter 1, Section 1.1 to 1.3.2, resulting in interlocutory decision dated Aug. 7, 2019, 6 pages.
"Integrating Electrical Heating Elements in Product Design," Metallic Resistance Heating Wire, Chapter 1, resulting in interlocutory decision dated Aug. 7, 2019, 1 page.
"Integrating Electrical Heating Elements in Product Design," Metallic Resistance Heating Wire, resulting in interlocutory decision dated Aug. 7, 2019, 8 pages.
International Preliminary Report on Patentability for Application No. PCT/AT2009/000413, dated May 5, 2011, 7 pages, Written Opinion for Application No. PCT/AT2009/000413, dated Jan. 25, 2010, 5 pages.
International Preliminary Report on Patentability for Application No. PCT/AT2009/000414, dated Apr. 26, 2011, 7 pages, Written Opinion for Application No. PCT/AT2009/000414, dated Jan. 26, 2010, 14 pages.
International Preliminary Report on Patentability for Application No. PCT/EP2012/003103, dated Feb. 6, 2014, 7 pages.
International Preliminary Report on Patentability for Application No. PCT/GB2014/051688, dated Dec. 17, 2015, 6 pages.
International Preliminary Report on Patentability for Application No. PCT/GB2015/050195, dated May 13, 2016, 17 pages.
International Preliminary Report on Patentability for Application No. PCT/GB2015/053445, dated Jan. 24, 2017, 19 pages.
International Preliminary Report on Patentability dated Sep. 9, 2014 for Application No. PCT/EP2013/64922, filed Jul. 15, 2013, 10 pages.
International Search Report and Written Opinion for Application No. PCT/GB2015/053445, dated Apr. 18, 2016, 21 pages.
International Search Report and Written Opinion dated Oct. 11, 2013 for Application No. PCT/EP2013/064922, filed Jul. 15, 2013, 6 pages.
International Search Report for App No. PCT/GB2015/050195, dated Sep. 2, 2015, 4 pages.
International Search Report for Application No. PCT/GB2014/051633, dated Dec. 4, 2014, 7 pages.
International Search Report for Application No. PCT/GB2014/051688, dated Aug. 26, 2014, 4 pages.
Notice of Allowance dated Oct. 18, 2019 for Korean Application No. 1020167018457, 2 pages (with translation—3 pages).
Notice of Allowance dated May 30, 2017 for Korean Application No. 1020157001277, 4 pages (No translation available).
Notice of Allowance dated Jun. 27, 2018 for Korean Application No. 1020167020977, 3 pages.
Notice of Opposition dated Oct. 30, 2019 for European Application No. 16166656.5, 39 pages.
Notice of Reasons for Rejection dated Oct. 15, 2013 for Japanese Application No. 2011532464, 6 pages.
Notice of Reasons for Revocation dated Apr. 17, 2017 for Japanese Patent No. 5960358, with English translation, 12 pages.
Notification of Transmittal of IPRP for International Application No. PCT/GB2014/051633 dated Oct. 23, 2015, 9 pages.
Notification to Grant Patent Right for Invention dated Oct. 25, 2018 for Chinese Application No. 201610086101.4, 2 pages.
Office Action and Search Report dated Feb. 28, 2019 for Japanese Application No. 2018-088088, 25 pages.
Office Action dated Sep. 3, 2014, for Russian Application No. 2013504605, 7 pages.
Office Action dated Jul. 2, 2020 for Chinese Application No. 201780020023.0 filed Sep. 25, 2018, 22 pages.
Office Action dated Nov. 21, 2017 for Russian Application No. 2016142584, 8 pages.
Office Action dated Nov. 22, 2016 for Canadian Application No. 2878951, 3 pages.
Office Action dated Sep. 22, 2017 for Russian Application No. 2015146847, 11 pages.
Office Action dated Nov. 23, 2018 for Korean Application No. 1020167018457, 6 pages (12 pages with translation).
Office Action dated Apr. 25, 2017 for Japanese Application No. 2016123816, 2 pages (No translation available).
Office Action dated May 12, 2017 for Korean Application No. 10-20157034538, 10 pages.
Office Action for European Application No. 16166656, dated Jul. 29, 2020, 7 pages.
Office Action for Chilean Application No. 201701486 dated Nov. 11, 2019, 10 pages.
Office Action for Chinese Application No. 201480031296.1 dated Mar. 27, 2017, 13 pages.
Office Action dated Jun. 2, 2016 for Chinese Application No. 201380038075.2, 7 pages (with translation—19 pages).
Office Action dated Dec. 12, 2018 for Korean Application No. 10-2017-7015164, 3 pages.
Office Action dated Jun. 15, 2018 for Korean Application No. 10-2017-7015164, 13 pages.
Office Action dated Mar. 16, 2020 for Chinese Patent Application No. 201610255788.X, filed Oct. 21, 2009, 21 pages.
Office Action dated Jan. 25, 2019 for European Application No. 17189951.1, 4 pages.
Office Action dated Jun. 26, 2018 for Japanese Application No. 2017-530762, 16 pages.
Office Action dated Nov. 26, 2019 for Brazilian Application No. 112015000872, 4 pages.
Office Action dated Sep. 27, 2019 for Korean Application No. 10-20197005785, 13 pages.
Office Action dated May 4, 2018 for Chinese Application No. 201610086101.4, 7 pages.
Office Action dated Apr. 10, 2019, for Korean Application No. 1020167018457, 13 pages.
Office Action dated Apr. 23, 2018 for Chinese Application No. 201580006377.0, 9 pages (20 pages with translation).
Office Action dated Dec. 8, 2017, for Korean Application No. 1020167020977, 13 pages.

(56) References Cited

OTHER PUBLICATIONS

Office Action dated Jan. 23, 2018, for Japanese Application No. 2016548373, 3 pages, (6 pages with translation).
Office Action dated Jun. 5, 2018, for Chinese Application No. 201610552323.0, 11 pages, (18 pages with translation).
Office Action dated Mar. 14, 2018, for Russian Application No. 2016131333, 7 pages (13 pages with translation).
Opposition Statement dated Mar. 30, 2017 for Japanese Patent No. 5960358, 144 pages (No translation available).
Partial EPO Opposition, resulting in interlocutory decision dated Aug. 7, 2019, 75 pages.
Search Report for Chilean Application No. 2019-11665, dated Nov. 11, 2019, 10 pages.
Search Report for Japanese Application No. 2011532464, dated Sep. 18, 2013, 116 pages.
Search Report for Japanese Application No. 2014-179732, dated Sep. 9, 2015, 12 pages.
Search Report for Japanese Application No. 2016134648, dated Mar. 28, 2017, 29 pages.
Search Report for Japanese Application No. 2016-564977, dated Oct. 25, 2017, 19 pages.
Search Report for Japanese Application No. 2011532464, dated Sep. 24, 2013, 53 pages.
Search Report dated Feb. 1, 2017 for Japanese Application No. 2016517671, 13 pages.
Search Report dated Apr. 14, 2017 for Japanese Application No. 2016-134648, 31 pages.
Search Report dated Sep. 19, 2013 for Japanese Application No. 2011-532464, 116 pages.
Search Report dated Jun. 24, 2019 for Russian Application No. 2018137583, 2 pages.
Search Report dated Apr. 25, 2018 for Chinese Application No. 201610086101.4, 1 page.
Search Report dated Aug. 25, 2015 for Japanese Application No. 2014-179732, 10 pages.
Search Report dated Apr. 29, 2019 for Russian Application No. 2018137501, 12 pages.
Search Report dated May 29, 2015 for Great Britain Application No. 1422018, 3 pages.
Search Report dated Mar. 20, 2015, for Great Britain Application No. GB1401520.0, 2 pages.
Sharafat et al., "Ceramic Foams: Inspiring New Solid Breeder Materials," 12th International Workshop on Ceramic Breeder Blanket Interactions, Germany, Sep. 16-17, 2004, 22 pages.
Supulveda et al., "Processing of Cellular Ceramics by Foaming and In Situ Polymerisation of Organic Monomers," Loughborough University, 1999, 22 pages.
Wires.co.uk, "Bare Nickel Chrome/Nichrome Section," Jun. 20, 2012, 33 pages.
Wires.co.uk, "Specialist in Craft Wire," Jun. 20, 2012, 5 pages.
Written Opinion for Application No. PCT/AT2012/000017, dated Jul. 3, 2012, 4 pages.
Written Opinion for Application No. PCT/GB2014/051633, dated Dec. 4, 2014, 11 pages.
Written Opinion for Application No. PCT/GB2014/051688, dated Aug. 26, 2014, 4 pages.
Written Opinion dated Jun. 23, 2014 for Application No. PCT/EP2013/064922, filed Jul. 15, 2013, 4 pages.
Written Opinion of the International Preliminary Examining Authority for Application No. PCT/GB2015/050195 dated Jan. 20, 2016, 8 pages.
Written Opinion of the International Searching Authority for Application No. PCT/GB2015/050195, dated Sep. 2, 2015, 8 pages.
Office Action For Chinese Application No. 201780020023.0, dated Mar. 8, 2021, 19 pages.
Notice of Reasons for Rejection for Japanese Application No. 2020-121265, dated Jul. 20, 2021, 8 pages.
Office Action For Korean Application No. 10-2018-7031081, dated Dec. 15, 2021, 6 pages.
Search Report for Japanese Application No. 2018-546893, dated Nov. 25, 2019, 27 pages.
European Search Report for Application No. 22155057.7, dated Jun. 15, 2022, 10 pages.
Notice of Reasons for Rejection for Japanese Application No. 2020-121265, dated Jun. 21, 2022, 8 pages.
Kynol, "Standard Specifications of Kynol Activated Carbon Fiber Products", published by Kynol.
Decision to Grant for Russian Application No. 2017105898, dated Mar. 16, 2018, 12 Pages (Official Copy Only).
"Feature Analysis of Claim 1", BATMark Limited, Opposition Against EP3117860B1, Exhibit D6, Oct. 30, 2019, 1 Page. (Official Copy Only).
Japanese Search Report, Application No. 2016-564977, dated Oct. 25, 2017, 19 pages (10 pages of English Translation and 9 pages Of Official Copy).
Letter from Patentee for European Application No. 17189951.1, dated Aug. 21, 2018, 11 Pages (Official Copy Only).
Notice of Opposition—Imperial Tobacco Limited for European Application No. 20171293.2, dated Nov. 16, 2022, 28 pages.
Notice of Opposition—Philip Morris for European Application No. 20171293.2, dated Nov. 17, 2022, 27 Pages.
Notice of Reasons for Rejection received for Japanese Application No. 2020-181572 dated Feb. 13, 2023, 29 Pages (14 Pages of English Translation and 15 Pages of Official Copy).
Notification to Grant received for Chinese Patent Application No. 201610256674.7. dated Jan. 12, 2023, 7 Pages (2 Pages of English Translation and 5 Pages of Official Copy).
Wikipedia , "Electronic Cigarette", Available at <https://en.wikipedia.org/w/index.phptitle=Electronic_cigratte&oldid=284227163>, April 2009, 7 Pages.

* cited by examiner

ELECTRONIC AEROSOL PROVISION SYSTEM AND VAPORIZER THEREFOR

PRIORITY CLAIM

The present application is a National Phase entry of PCT Application No. PCT/GB2017/051139, filed Apr. 25, 2017, which claims priority from U.K. Patent Application No. GB 1607322.3, filed Apr. 27, 2016, each of which is hereby fully incorporated herein by reference.

TECHNICAL FIELD

The present disclosure relates to aerosol provision systems and vaporizers for use in aerosol provision systems.

BACKGROUND

Vapor or aerosol provision systems and devices, such as electronic cigarettes, typically include a reservoir of a source liquid, perhaps including nicotine, and a heater or heating element powered by a battery which acts to vaporize the source liquid for inhalation by a user. A wick may be used to deliver source liquid to the heating element for the vaporization process. For example, the heating element may be a wire coil wrapped around a central wick.

An aim of these arrangements is to maximize the amount of vaporized source liquid delivered with each inhalation (puff). This can be achieved by increasing the heat output of the heating element so that more source liquid is vaporized during the duration of a puff. Reducing the electrical resistance of the heater, for example by using a lower resistance wire to form a heating element, allows more current to flow for a given battery voltage, thereby increasing the power consumed by the heater and generating more heat. This approach leads to particular challenges, however.

To lower the resistance one may increase the diameter of the heating wire. An increased amount of source liquid should be delivered by the wick to feed the higher vaporization rate enabled by the higher heater power; this requires a larger size of wick. These factors can reduce efficiency, however, because of heat conduction from the heater into the wick material, and the requirement to heat a larger mass of heater.

Also, achievable rates of vapor production may be limited by the speed at which vapor moves into the inhalable airstream. Vaporization of the source liquid occurs at the interface of the heater and the wick. With a central wick inside a heater coil, the vapor has to travel from the interface out beyond the heater surface to be collected for inhalation. A reduced heater resistance to increase the power combined with the limited interface area may create a vaporization so intense that the vapor cannot escape quickly enough and instead forms pockets at the interface that impede liquid contact with the heater. This reduces the efficiency of vapor production, causing the heater temperature to rise because the power is not being utilized for vaporization. This can degrade the quality of the vapor and may lead to undesirable by-products.

SUMMARY

Alternative wick and heater arrangements are therefore of interest.

According to a first aspect of some embodiments described herein, there is provided a sub-assembly for an electronic vapor provision system comprising: a source of liquid for vaporization; and a vaporizer for vaporizing a portion of the liquid for inhalation by a user, the vaporizer comprising: a wick component; and an electrical heating element embedded in the wick component; wherein the wick component comprises a sheet of a porous electrically-insulating material and is arranged to wick liquid from the source of liquid to a surface of the wick component adjacent to the embedded electrical heating element for vaporization.

The porous electrically-insulating material may comprise a porous ceramic. The wick component may have a porosity in the range of 30% to 85%, and may have a thickness at least 50 times less than a longest dimension of the wick component.

The heating element may have an embedded shape including one or more bends and a length embedded in the wick component of between 2 and 20 times the longest dimension of the wick component. The one or more bends may define adjacent portions of the heating element that have a centre-to-centre spacing not greater than twice an embedded width of the heating element. The thickness of the wick component may be in the range of 105% to 250% of an embedded width of the heating element. The heating element may be embedded substantially centrally with respect to the thickness of the wick component. The heating element may comprise a metallic wire.

The wick component may be substantially planar. The vaporizer may be supported in a vaporization chamber by one or more parts of the wick component passing through apertures in one or more walls of the vaporization chamber to extend into the source of liquid. One or more parts of the wick component that pass through apertures in one or more walls of the vaporization chamber may be at opposite sides of the wick component. The vaporizer may be supported in the vaporization chamber such that a thinnest profile of the wick component is presented to a direction of airflow through the vaporization chamber. The source of liquid may comprise a reservoir having an annular shape and surrounding the vaporization chamber. The wall of the vaporization chamber may also be an inner wall of the reservoir.

The sub-assembly may be a cartomizer for an electronic vapor provision system.

According to a second aspect of some embodiments described herein, there is provided an electronic vapor provision system comprising a sub-assembly according to the first aspect.

According to a third aspect of some embodiments described herein, there is provided a method of making a vaporizer for an electronic vapor provision system, the method comprising: forming an electrically conductive heating element; arranging powdered ceramic material around the heating element in a desired shape for a wick component; and sintering the ceramic material to form a porous ceramic wick component with the heating element embedded therein.

According to a fourth aspect of some embodiments described herein, there is provided a method of making a vaporizer for an electronic vapor provision system comprising: forming an electrically conductive heating element; arranging the heating element between a first layer and a second layer of sheet porous electrically-insulating material; and bonding the first layer and the second layer together to form a porous wick component with the heating element embedded therein.

In the method aspects, forming the conductive heating element may comprise shaping a metallic wire or depositing a conductive ink into a path with one or more bends, and a length between 2 and 30 times the intended longest dimension of the wick component. The one or more bends may define adjacent portions of the wire that have a centre-to-centre spacing not greater than twice a width of the wire. The methods may further comprise mounting the completed vaporizer in a vaporization chamber by passing one or more edges of the wick component through one or more apertures in a wall of a vaporization chamber.

According to a fifth aspect of some embodiments described herein, there is provided an electronic vapor provision device including a reservoir for source liquid and a vaporization chamber adjacent the reservoir in which source liquid can be vaporized, the vaporization chamber housing a vaporizer comprising: a porous ceramic wick component; and a metallic heater element embedded in the wick component and connectable to a battery in the electronic vapor provision device; wherein two ends of the wick component pass through apertures in walls of the vaporization chamber to suspend the vaporizer across the vaporization chamber, the two ends penetrating into the reservoir to absorb source liquid and transport it to the heating element by capillary action through pores in the wick component.

These and further aspects of certain embodiments are set out in the appended independent and dependent claims. It will be appreciated that features of the dependent claims may be combined with each other and features of the independent claims in combinations other than those explicitly set out in the claims. Furthermore, the approach described herein is not restricted to specific embodiments such as set out below, but includes and contemplates any appropriate combinations of features presented herein. For example, an electronic cigarette, a sub-assembly or a vaporizer may be provided in accordance with approaches described herein which includes any one or more of the various features described below as appropriate.

BRIEF DESCRIPTION OF THE DRAWINGS

Various embodiments will now be described in detail by way of example only with reference to the accompanying drawings in which.

DETAILED DESCRIPTION

Aspects and features of certain examples and embodiments are discussed/described herein. Some aspects and features of certain examples and embodiments may be implemented conventionally and these are not discussed/described in detail in the interests of brevity. It will thus be appreciated that aspects and features of apparatus and methods discussed herein which are not described in detail may be implemented in accordance with any conventional techniques for implementing such aspects and features.

The present disclosure relates to aerosol provision systems, also referred to as vapor provision systems, such as e-cigarettes. Throughout the following description the term "e-cigarette" or "electronic cigarette" may sometimes be used; however, it will be appreciated this term may be used interchangeably with aerosol (vapor) provision system or device.

Figure 1:
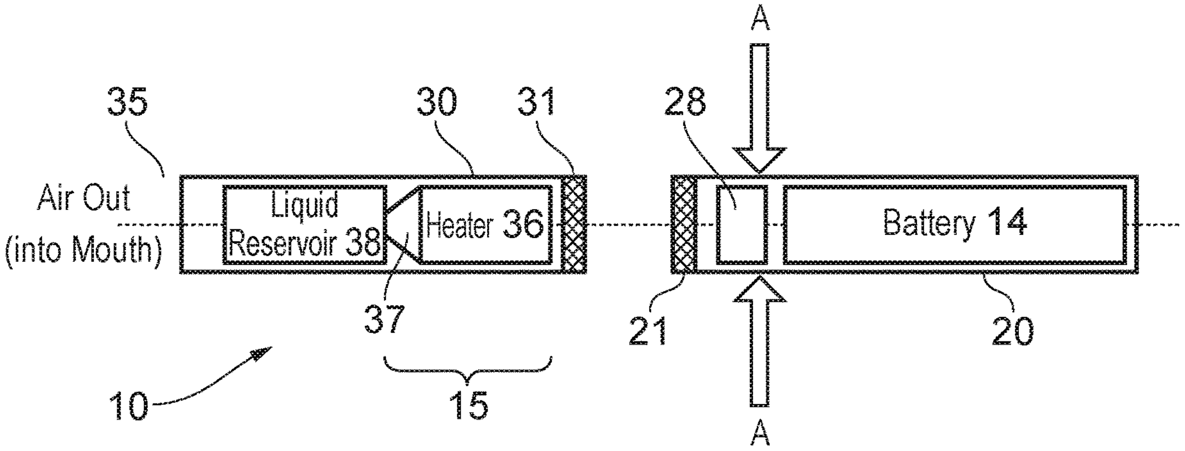
FIG. 1 shows a schematic representation of an electronic cigarette with which a vaporizer according to embodiments of the disclosure may be used.

FIG. 1 is a highly schematic diagram (not to scale) of an example aerosol/vapor provision system such as an e-cigarette 10 to which embodiments are applicable. The e-cigarette 10 has a generally cylindrical shape, extending along a longitudinal axis indicated by a dashed line (although aspects of the disclosure are applicable to e-cigarettes configured in other shapes and arrangements), and comprises two main components, namely a body 20 and a cartridge assembly 30.

The cartridge assembly 30 includes a reservoir or source of liquid 38 containing a source liquid comprising a liquid formulation from which an aerosol is to be generated, for example containing nicotine, and a heating element or heater 36 for heating source liquid to generate the aerosol. A wicking element or component or wick 37 is provided to deliver source liquid from the reservoir 38 to the heating element 36. A part or parts of the wick 37 are in fluid communication with source liquid in the reservoir 38 and by a wicking or capillary action source liquid is drawn along or through the wick 37 to a part or parts of the wick 37 which are in contact with the heater 36. Vaporization of the source liquid occurs at the interface between the wick 37 and the heater 36 by the provision of heat energy to the source liquid to cause evaporation, thus generating the aerosol. The source liquid, the wick 37 and the heater 36 may be collectively referred to as an aerosol or vapor source. The wick 37 and the heater 36 may be collectively referred to as a vaporizer or an atomizer 15. An atomizer/vaporizer may be arranged in a chamber or housing which is substantially sealed from the reservoir of source liquid to prevent or limit leakage of the source liquid into the chamber. The wick is the intended path for liquid from the reservoir to the heater. The inclusion of the vaporizer/atomizer within the cartridge assembly leads to the term "cartomizer" which is sometimes applied to this component of an electronic cigarette.

The cartridge assembly 30 further includes a mouthpiece 35 having an opening through which a user may inhale the aerosol generated by the vaporizer 15. The aerosol for inhalation may be described as an aerosol stream or inhalable airstream. As an example, the source liquid may comprise around 1 to 3% nicotine and 50% glycerol, with the remainder comprising roughly equal measures of water and propylene glycol, and possibly also comprising other components.

The body 20 includes a re-chargeable cell or battery 14 (referred to herein after as a battery) to provide power for the e-cigarette 10, and a printed circuit board (PCB) 28 and/or other electronics for generally controlling the e-cigarette 10. The body can therefore also be considered as a battery section, or a control unit or section. In use, when the heater 36 receives power from the battery 14, as controlled by the circuit board 28 possibly in response to pressure changes detected by an air pressure sensor (not shown), the heater 36 vaporizes source liquid delivered by the wick 37 to generate the aerosol, and this aerosol stream is then inhaled by a user through the opening in the mouthpiece 35. The aerosol is carried from the aerosol source to the mouthpiece 35 along an air channel (not shown in FIG. 1) that connects the aerosol source to the mouthpiece opening as a user inhales on the mouthpiece. To this end, the vaporizer 15 may be accommodated in a vaporizer chamber (not shown) that is comprised within, or otherwise connected to, an airflow pathway through the e-cigarette 10.

In this particular example, the body 20 and cartridge assembly 30 are detachable from one another by separation in a direction parallel to the longitudinal axis, as shown in FIG. 1, but are joined together when the device 10 is in use by cooperating engagement elements 21, 31 (for example, a screw or bayonet fitting) to provide mechanical and electrical connectivity between the body 20 and the cartridge assembly 30, in particular connecting the heater 36 to the battery 14. An electrical connector interface on the body 20 used to connect to the cartridge assembly 30 may also serve as an interface for connecting the body 20 to a charging device (not shown) when the body 20 is detached from the cartridge assembly 30. The other end of the charging device can be plugged into an external power supply, for example a USB socket, to charge or to re-charge the battery 14 in the body 20 of the e-cigarette. In other implementations, a separate charging interface may be provided, for example so the battery 14 can be charged when still connected to the cartridge assembly 30.

The e-cigarette 10 is provided with one or more holes (not shown in FIG. 1) for air intake, indicated by the arrows A. These holes, which are in an outer wall of the body 20 (but which in other examples may be in an outer wall of the cartridge assembly 30), connect to an airflow path through the e-cigarette 10 to the mouthpiece 35. The airflow path may include a pressure sensing region (not shown in FIG. 1) in the body 20, and then connects from the body 20 into cartridge assembly 30 to a region (such as the vaporizer chamber) around the heating element 36 so that when a user inhales through the mouthpiece 35, air is drawn into the airflow path through the one or more air inlet holes. This airflow (or the resulting change in pressure) is detected by a pressure sensor (not shown in FIG. 1) in communication with the airflow path that in turn activates the heater 36 (via operation of the circuit board 28) to vaporize a portion of the source liquid at the wick-heater interface to generate the aerosol. The airflow passes through the airflow path, and combines with the vapor in the region around the heater 36, and the resulting aerosol (combination of airflow and condensed vapor) travels as an aerosol stream along the airflow path connecting from the region of the heater 36 to the mouthpiece 35 to be inhaled by a user.

In some examples, the detachable cartridge assembly 30 may be disposed of when the supply of source liquid is exhausted, and replaced with another cartridge assembly if so desired. In other examples the reservoir may be refillable with more source liquid. The body 20 may be intended to be reusable by recharging of the battery, for example to provide operation for a year or more by connection to a series of disposable detachable cartridges assemblies. In other examples, both the cartridge assembly 30 and the body 20 may be disposable, and may not be detachable from each other. Also, the various components may be located differently from the FIG. 1 example, and the cartridge assembly 30 and the body 20 may be connectable in a different configuration such as a side-by-side arrangement instead of the longitudinal arrangement of FIG. 1. Embodiments of the disclosure are applicable to these and other various alternatives.

According to embodiments of the disclosure, it is proposed to configure the vaporizer (atomizer) by embedding the heating element inside a porous wick component.

Figure 2:
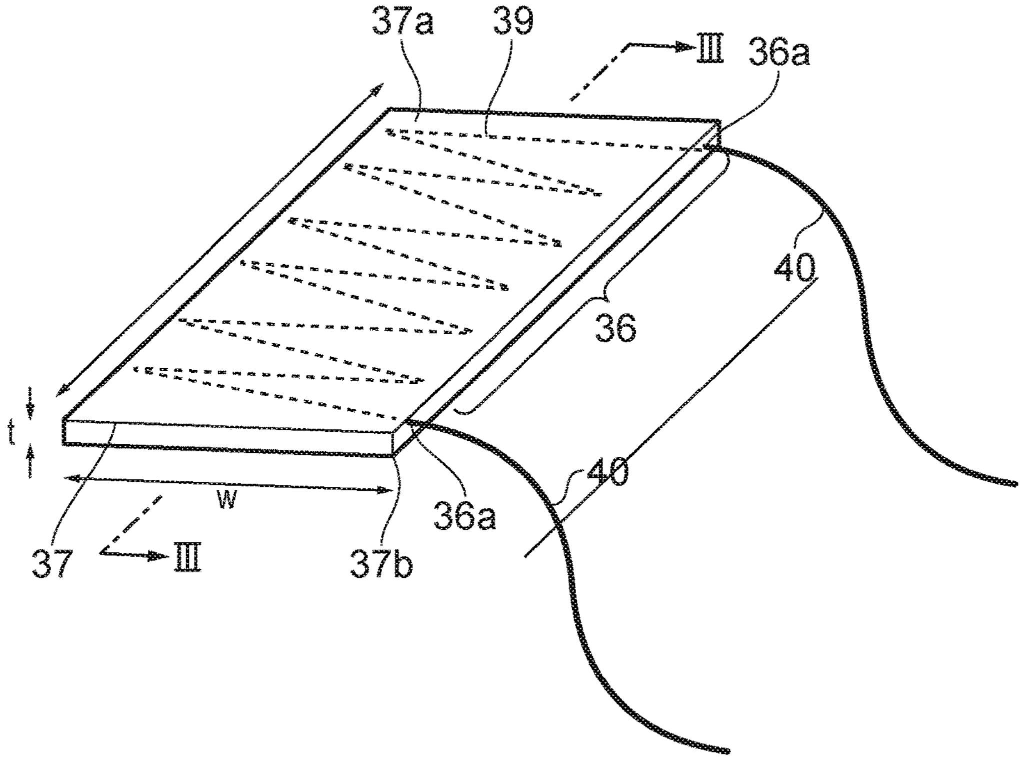
FIG. 2 shows a perspective view of an example vaporizer.

FIG. 2 shows a perspective view of a vaporizer 15 according to a first example embodiment. The wick or wicking element or component 37 is a thin flat planar substrate of an electrically-insulating porous material such as porous ceramic, having a thickness t, a length l and a width w. Embedded within the wick 37 is a heating element 36 in the form of a conductive (metallic) wire 39. This is shown in a phantom dotted line to indicate its position inside the wick. Each end 36*a* of the heating element 36 terminates at an edge of the wick 37 in a connecting lead 40 by means of which the heating element 36 can be connected (typically via an arrangement of contacts and other electrical wires and connections, and under control of a PCB or other control electronics) to an electrical power supply within an e-cigarette, such as the battery 14 in FIG. 1. The leads 40 and the wire 39 can be formed from a single length of wire, or may be separately fabricated and then connected for example by welding (such as for ease of fabrication or to utilize particular properties of different wires).

The heating element wire 39 is formed into a serpentine or zigzag shape between its two ends 36*a*. The wire formation occupies a single plane which is arranged substantially mid-way through the thickness t of the wick 37 so as to be substantially equidistant from the upper 37*a* and lower 37*b* (with reference to the illustrated orientation) surfaces of the wick 37 (main surfaces). In this way, heat from the heating element 36 when powered by electric current can be delivered roughly equally to each main surface 37*a*, 37*b*. If the zig-zags or adjacent turns of the wire 39 are closely spaced so that all parts of the wick substrate are relatively close to part of the wire, heat can be delivered rapidly to all parts of the wick. A larger spacing between wire turns may lead to a wasted volume of wick material that takes up heat energy but does not attain a sufficient temperature for vaporization.

Figure 3:
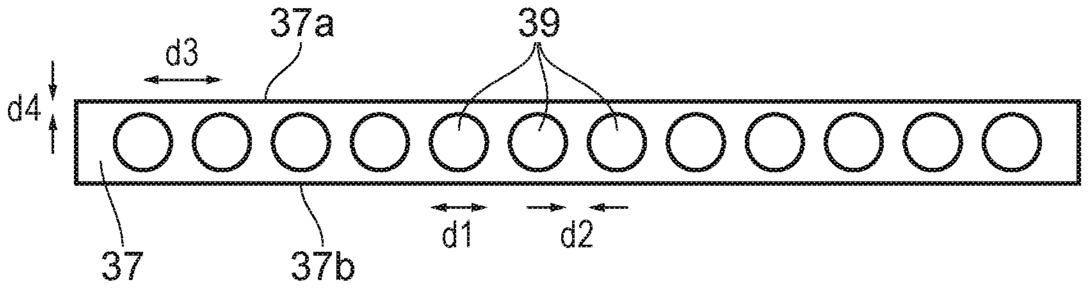
FIG. 3 shows a cross-sectional view through the example vaporizer of FIG. 2.

FIG. 3 shows a cross-sectional view through the vaporizer of FIG. 2, along the line III. From this, the dense packing of the adjacent sections of the wire 39 inside the volume of the wick 37 is apparent. The wire 39 occupies a substantial proportion of the total volume of the vaporizer. Adjacent portions of the wire are separated by a distance d2 less than the width d1 (diameter) of the wire. Hence, the center-to-center spacing d3 between adjacent wire portions is less than twice the wire width (2×d1). Also, the depth or thickness d4 of wick material between the main surfaces and the wire surface is less than the width of the wire d1. This thickness can be chosen having regard to the vaporization rate; if there is too great a depth of wick material vaporization will be impeded and insufficient vapor will escape from the wick surface. The disclosure is not limited to the above proportions, however, and greater or lesser size ratios may be used. The relative volumes and dimensions of the heater and the wick, the depth of wick material overlying the heater wire and the porosity of the wick material can be variously selected to deliver a sufficient volume of source liquid to feed the available vaporization rate while also allowing the vapor to escape from the wick material at a fast enough rate. For example, the embedded heater may have a volume that is at least 50% of the combined volume of the embedded heater and the wick (defined by the outer dimensions of the wick element), or between 40% and 60%, or between 30% and 70%. Alternatively, the combined volume may be confined to a zone of the wick over which the heater extends, for example a central zone or an end zone, with a relatively large further amount of the wick extending beyond this zone such as to ensure a significant wick volume reaching into a reservoir, or to reach the walls of the vaporization chamber if it is desired for vaporization to be kept remote from the walls. The part of the wick within which the heater is embedded (the combined volume) can be considered as a heating zone, where all or most of the vaporization occurs. The heating zone may comprise all or most of the wick, or just a part of it.

In this example the wick 37 is formed from a rigid porous ceramic material. The pores of the ceramic allow a wicking action so that when part of the wick is placed in fluid communication with a source liquid reservoir, source liquid in the reservoir is drawn through the pores to the wire 39. When the heater 37 is activated, heat is transferred to source liquid in direct contact with the wire 39 and also via intervening wick material. The resulting vapor passes through the pores to the wick surfaces 37*a*, 37*b* and out into the surrounding air to be collected by air flowing in the airflow path.

The wire 39 is embedded within the wick substrate 37. By "embedded" is meant that the material of the wick wholly covers and is in contact with substantially all the outer surface of the wire within the volume of the wick (subject to gaps where pores in the wick material are immediately adjacent to the wire). At each axial cross-sectional position along the wire, the porous ceramic material is in contact with the wire around its full circumference; the wire is wholly enveloped in the wick material. This contact between the wire and the wick is the interface at which the majority of the vapor formation happens, so an embedded configuration maximizes the interface area for a given length of wire, and greatly increases the interface area compared with vaporizer arrangements in which a coiled heater wire is wrapped around a central wick, for example. A thinner wire with more turns or bends (to increase the length) might provide a larger interface area but this may need to be balanced against the beneficial lower resistance and higher power output of a thicker wire.

Although a fully embedded arrangement in which the wick material covers the wire completely gives a maximum vaporization interface, a partially embedded configuration in which the heating element is at least partly exposed at one or both main surfaces of the wick substrate might be considered useful in some circumstances.

The heating element in the form of a wire 39 can be fabricated in any shape between the two ends 36*a*. A shape which maximizes the length of the wire that can be accommodated within the wick volume gives a largest vaporization interface; this might be achieved by any convoluted path between the two ends. Such a path has a non-linear shape. For example, the shape may be an angular or a curved serpentine shape, an angular or curved zig-zag, or an angular or curved spiral, and the shape may be regular (repeating) or irregular. Incorporation of a plurality of turns, bends or corners into the shape will increase the available length. In some embodiments, the embedded conductive length of the heating element between its two ends is several or many times the longest dimension of wick element, achieved by including a plurality of turns, bends, corners or folds along the length in the heating element. For example, the heating element may have a length which is between 2 and 20 times or between 5 and 10 times the length of the longest dimension (edge) of the wick element. The two ends may be located at edge surfaces of the wick (the same edge, as in FIG. 2, or different edges) or on one or both main surfaces (which may be convenient for a spiral or other shape where the heating element terminates away from a wick edge). The adjacent lengths of the wire may be as closely spaced as is conveniently achievable with the chosen manufacturing process and materials for fabricating the vaporizer, to maximize the length of useable wire. However, care should be taken that no parts of the wire are touching each other within the wick, so as to avoid an electrical short circuit. A complex shape is not essential, though, and the wire may be substantially straight (linear) or gently curving between its two ends if this is deemed to deliver sufficient heating power, or if an elongate wick is preferred. This might provide a heating element that is between 1 and 2 times the length of the wick's longest side, for example.

Figure 4A:
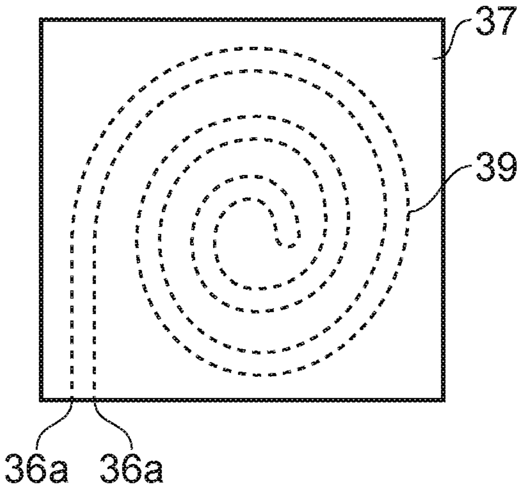
FIGS. 4*a*, 4*b* and 4*c* show schematic plan views of further example vaporizers.
Figure 4B:
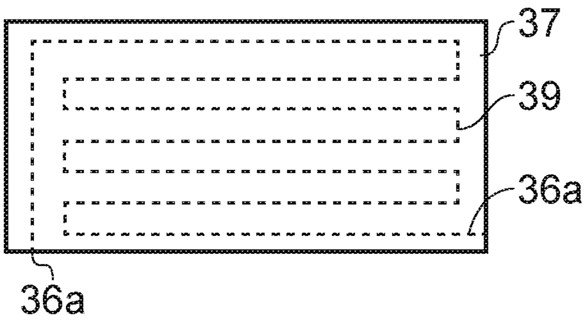
Figure 4C:
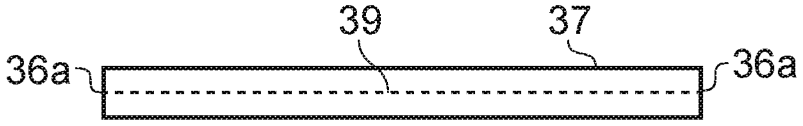

FIGS. 4*a*, 4*b* and 4*c* show schematic plan views of various examples of vaporizers with differently shaped heating element wires. The example of FIG. 4*a* has a square wick element 37 and a heating wire 39 arranged as a double spiral so that both ends 36*a* can be located at the same edge of the wick. The connecting leads are omitted for simplicity. The example of FIG. 4*b* has a rectangular wick element 37 and a heating wire 39 in an angular, cornered, shape that is folded back on itself a plurality of times. The ends 36*a* are on different edges of the wick 37. The example of FIG. 4*c* shows a highly linear wick element 37, having a length many times greater than its width, and a heating wire 39 configured as a simple straight line between its two ends 36*a* at opposite short edges of the wick 37.

The heating element need not be formed from conductive wire (such as by bending). An appropriate shape that provides a conductive path of the desired length might be stamped, cut or pressed out of sheet metal, or a metallic ribbon (rather than a wire) might be bent into a suitable shape, for example.

Suitable conductive materials for the heating element include any resistive metal, for example nichrome, steel, titanium or other metals and metal alloys. Other materials may also be used, such as conductive ink (non-metal or metal based), printed, drawn or deposited along a suitably shaped path.

The wick element may have various properties. It is formed from a porous material to enable the required wicking or capillary effect for drawing source liquid through it from a source liquid reservoir (where the wick meets the source liquid at a reservoir contact site) to the vaporization interface. Porosity is typically provided by a plurality of interconnected or partially interconnected pores (holes or interstices) throughout the material, and open to the outer surface of the material. Any level of porosity may be employed depending on the material, the size of the pores and the required rate of wicking. For example a porosity of between 30% and 85% might be selected, such as between 40% and 70%, between 50% and 80%, between 35% and 75% or between 40% and 75%. This might be an average porosity value for the whole wick element, since porosity may or may not be uniform across the wick. For example, pore size at the reservoir contact site might be different from pore size nearer to the heater.

The wick element has a substantially thin flat shape. For example it may be considered as a sheet, layer, film, substrate or the like. By this it is meant that a thickness of the wick (the dimension tin FIG. 2) is less or very much less than at least one of the length (1 in FIG. 2) and the width (w in FIG. 2) of the wick. Thus, the wick thickness (its smallest dimension) is less or very much less than the longest dimension. This enables the heating element to be close to the main surfaces of the wick, with the depth of overlying wick material being slight. The thickness may or may not be substantially uniform. For example, the wicking rate may be modified by a reduced or increased thickness at the reservoir contact site compared with the remainder of the wick. The wick may be planar, as in FIGS. 2 and 3, but its shape is not limited in this regard. The "flat" characteristic is intended to have a topological definition, in that the wick may form a curved surface such a cylinder (tube), a trough or a segment of a spherical surface or other dish-like form. The thickness of the wick may, for example, be in the range of 105% to 250% of the thickness of the heater element (the diameter of a wire used as the heater element, for example), such as between 105% and 200%, or 105% and 150%, or 110% and 200%, or 110% and 150%, or 120% and 200%, or 120% and 150%. The thickness of the wick may, for example, be in the range 50 to 200 times less than the longest dimension of the wick (typically the length). For example the length l might be 50 to 150 times the thickness t, or 50 to 100 times, or 50 to 150 times, or 100 to 150 times, or 100 to 200 times. As an example, the wick might be rectangular with a length l in the range 5 mm to 15 mm, a width w in the range 5 mm to 15 mm, and a thickness t somewhat in excess of a wire thickness of 0.1 mm, such as 0.12 mm to 0.2 mm. The disclosure is not limited in this regard, however, and other dimensions, shapes and proportions of the wick may be used.

It is useful for the wick to have sufficient rigidity to support itself in a required position within the vapor source. For example, it may be mounted at or near one or two edges and be required to maintain its position substantially without flexing, bending or sagging. The rigidity may arise from the wick material in the selected wick thickness (so that an appropriate thickness is used to provide this characteristic), and where the wick is able also to support the heater embedded in it. In other examples, some structural rigidity may be derived from the heater itself, so that the heater aids in supporting the mounted wick in its required position. The overall rigidity of the wick and heating element combination may be relied upon, or the rigidity of the wick alone. The term rigid is considered to imply that the wick or vaporizer is substantially non-flexible or non-pliant.

As an example, porous ceramic is a useful material to use as the wick element. Any ceramic with appropriate porosity may be used. However, the disclosure is not so limited, and any electrically-insulating material having the same or similar properties or characteristics might be used. In general, the porous material should be considered as a "solid" or "hard" material, in contrast to "soft" fabric and fibrous materials, such as cotton and other fibers which are often used in the art as wicks and to absorb stores of source liquid in place of a reservoir of free-flowing liquid. In this context, the solid wick material is substantially non-compressible.

A vaporizer of the kind described herein may be fabricated in a straightforward manner. If porous ceramic is chosen as the porous wick material, this is available as a powder which can be formed into a solid by sintering (heating to cause coalescence, possibly under applied pressure). Thus, the heating element can be fabricated first (bending a wire into the appropriate shape, for example), and the ceramic powder can be arranged around the heating element in the desired shape, such as by filling a mould that has the heating element suspended or otherwise arranged inside it. Sintering then solidifies the ceramic to create the porous wick, with the heating element embedded in it. Fabricating the vaporizer in this way, by forming and shaping the wick element from wick material around the heating element, achieves the required embedded arrangement, giving close contact between the heating element and the wick at the vaporization interface.

Alternatively, the vaporizer may be formed from two separate layers of wick material with the heating element sandwiched between the two layers. After stacking the layers, the wick layers may be secured around the heating element by gluing, welding or other bonding methods, according to what is appropriate to the chosen wick material. The wick layers may be the same thickness, or different thicknesses. The heating element may be preformed to the desired shape, as mentioned above, or in the case of conductive ink, can be drawn or printed onto the surface of one wick layer before bonding the second wick layer on top.

A vaporizer in accordance with aspects of the disclosure may be used in conjunction with a reservoir of free flowing source liquid (although it may be combined with a reservoir of the type that is formed from a soft porous material such as cotton which is soaked with source liquid). It is envisaged that the vaporizer will be housed inside a vaporizer chamber which communicates with or forms part of the airflow channel through an electronic cigarette but which is substantially sealed against the ingress of free source liquid from an adjacent reservoir. The wick of the vaporizer forms the path for source liquid to enter the vaporizer chamber; this is achieved by arranging that a part of the wick (one or more edges, for example) extends through a wall of the chamber into the reservoir. A seal can be arranged around the wick where it traverses the wall, to limit leakage into the chamber. The part of the wick including the embedded heating element lies inside the chamber so that air flowing along the airflow channel can pick up vaporized source liquid given off from the vaporizer when the heating element is activated (electrical current is passed through it).

Figure 5A:
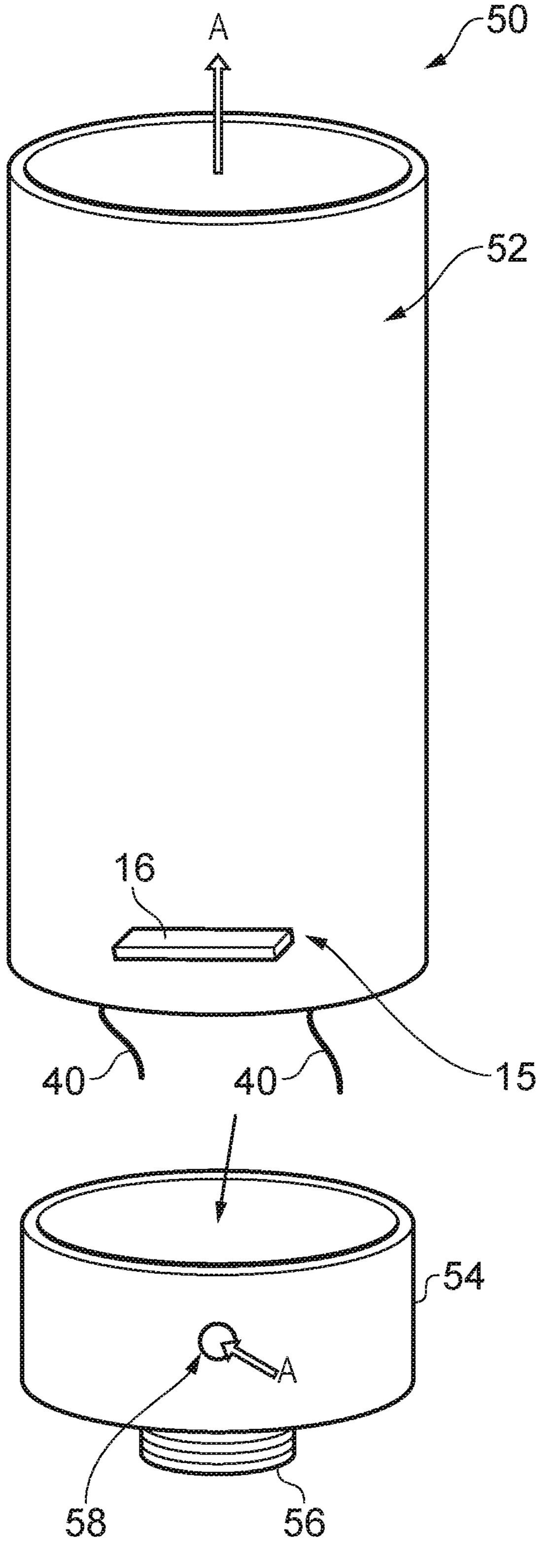
FIG. 5A shows a perspective exploded side view of an example vaporization chamber having a vaporizer.

FIG. 5A shows a perspective side view of an example vaporization chamber 50. The chamber 50 has walls defined by a hollow tube 52 (cylindrical in this example, but other cross-sectional shapes may be used if preferred). The tube 52 is part of the air flow path through the electronic cigarette, and the aerosol stream carrying the vaporized source liquid exits the end of the tube as shown by the arrow A, to enter a next part of the air flow path for travel to the electronic cigarette's mouthpiece (not shown). At its lower end (as illustrated) the tube 52 is sealable by being joined to base portion 54 (indicated by the small arrow). The base portion 54 has a screw thread connector 56 for mechanical and electrical connection to a battery section (not shown). The base portion 54 has an air inlet 58 by which air is drawn into the vaporization chamber 50 when a user inhales on the electronic cigarette. One or more air inlets 58 may be provided, possibly in locations other than on a separate base portion 54, and they may be provided with an adjustment mechanism to deliver variable ventilation into the electronic cigarette. The base portion 54 need not be separate from the tube 52; the two components may be formed integrally.

A vaporizer 15 according to aspects of the disclosure is disposed inside the vaporization chamber 50. The wick element of the vaporizer 15 has an elongate shape (a rectangle in this example) which is longer than the width (diameter) of the tube 52. Thus, the wick extends across the full width of the tube and beyond, so that opposite end portions 16 of the wick pass through the tube walls in a sealed configuration and lie outside the vaporization chamber 50. The vaporizer is thus suspended across the vaporization chamber. One end portion 16 can be seen in FIG. 5A protruding from the chamber wall. Electrical connection leads 40 are connected to the heating element at parts of the wick inside the chamber, so that they can be connected appropriately in the base portion 54 to receive current from a battery via the screw thread connector 56. In this way, air drawn in through the air inlet 58 passes over and past the vaporizer 15 as it travels along the tube 52, thereby collecting vapor to form the aerosol stream.

Figure 5B:
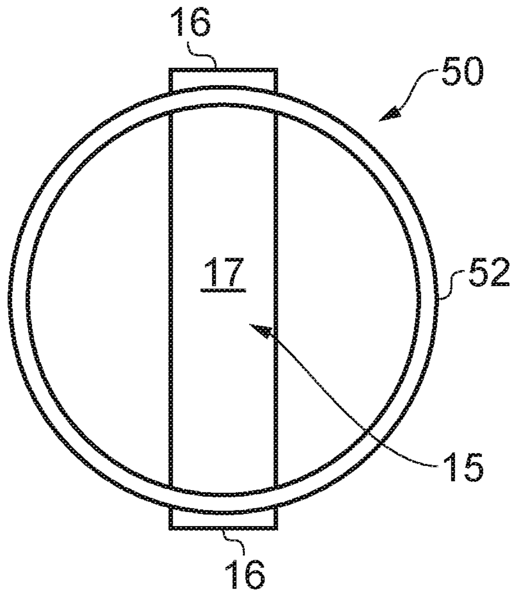
FIG. 5B shows an end view of the vaporization chamber of FIG. 5A.

FIG. 5B shows a view of the vaporization chamber looking into the tube 52 along its length. The vaporizer 15 can be seen mounted through opposite apertures in the tube walls such that its central part 17 is inside the chamber, extending fully across the tube 52, and its opposite ends 16 are outside the chamber. In an example, the protruding end portions have a protruding length of up to 2 mm, for example between 1 and 2 mm.

The ends of the wick are arranged to protrude through the walls of vaporization chamber so that they can carry source liquid to the heating element. This is achieved by locating a reservoir for the source liquid externally to the vaporization chamber.

Figure 6A:
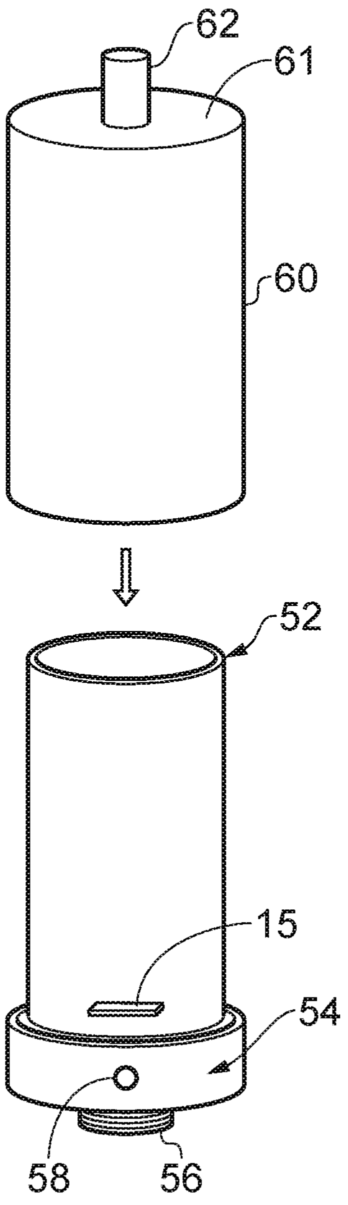
FIG. 6A shows a perspective exploded side view of a vapor source comprising the vaporization chamber of FIG. 5A.

FIG. 6A shows a perspective view of parts of a vapor source comprising a reservoir, and the vaporization chamber 50 and vaporizer 15 of FIG. 5A. An outer tube 60 of larger width (diameter) than the tube 52 forming the vaporization chamber walls is provided, and is sized to fit over and around the tube 52 as shown by the arrow, leaving an annular space between the inside of the outer tube 60 and the outside of the inner tube 52. The outer tube 60 may or may not form part of the outer surface of the electronic cigarette. The outer tube 60 connects to the vaporizer base portion 54 which acts to seal a first (lower, as illustrated) end of the annular space. The outer tube 60 is closed at its second (upper, as illustrated) end by a top wall 61, through which extends an outlet tube 62 which is in airflow communication with the interior of the inner tube 52 to enable the aerosol stream to leave the vaporization chamber. The outlet tube 62 may form the mouthpiece of the electronic cigarette, or may be an intermediate section of the air flow path that leads towards the mouthpiece.

The annular space defined between the outer tube 60 and the inner tube 52 is sealed to make it substantially leak-proof. It forms a reservoir for free-flowing source liquid, which can exit the reservoir only via capillary action along the wick of the vaporizer 15 (assuming no accidental or unintended leaks). The protruding ends 16 of the wick lie inside the reservoir, and hence absorb source liquid that is stored in the reservoir.

Figure 6B:
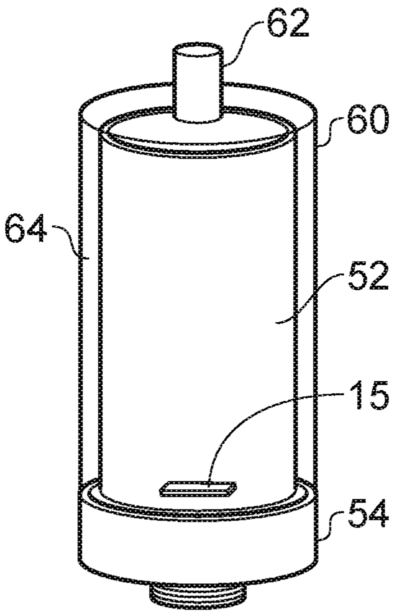
FIG. 6B shows a perspective side view of the vapor source of FIG. 6A.

FIG. 6B shows a perspective view the vapor source of FIG. 6A in assembled form, when the outer tube 60 has been placed over the inner tube 52 and connected to the base 54, thereby defining the reservoir 64 in the intervening annular space. In this example the outer tube 60 forms the outside of the electronic cigarette and is made from a transparent material, and the inner tube 52 and vaporizer 15 are visible through it. This feature allows visibility of source liquid in the reservoir also, so a user can determine how much source liquid there is. In other examples the outer tube 60 can be made from opaque material, and/or may have a casing around it, so that the reservoir contents cannot be seen.

The FIGS. 6A and 6B device is merely an example, and the vaporizer may be mounted in a vaporization chamber in any way that allows at least one part of it to reach into a reservoir to wick source liquid. The wick may extend wholly or partly across the vaporization chamber. Either ends or edges (one or more) may extend through the chamber wall(s). Opposite ends or edges or adjacent ends or edges may be used for this. The extension through the wall(s) conveniently provides support for the vaporizer, and its level of rigidity may determine how much or many of its edges should be used in this way. Also, the rate at which source liquid needs to be transferred by the wick from the reservoir to the heating element will determine what proportion of the wick should extend into the reservoir. Two or more opposite or non-adjacent ends or edge parts may be considered useful since this increases the likelihood of contact between the wick and source liquid when the reservoir is partially empty, for example when the electronic cigarette is held at an angle. The vaporizer may be mounted so that the plane of the wick is orthogonal to the main air flow direction through the vaporization chamber (as in FIGS. 5A, B and 6A, B). Alternatively, it may be mounted with its plane parallel to the air flow direction (imagine the vaporizer for FIG. 5A rotated 90 degrees about its longitudinal axis), thereby presenting the smallest (thinnest or narrowest) profile of the wick element to the direction of air flow through the chamber. A parallel arrangement allows a larger vaporizer to be accommodated in the vaporization chamber with less impediment to air flow (which would affect the "draw" as perceived by the inhaling user). Indeed, a parallel mounting allows a wick area inside the vaporization chamber to be up to the size of the longitudinal cross-sectional area of the chamber, maximizing the surface available for delivering vapor, and hence the aerosol production per puff.

Figure 7:
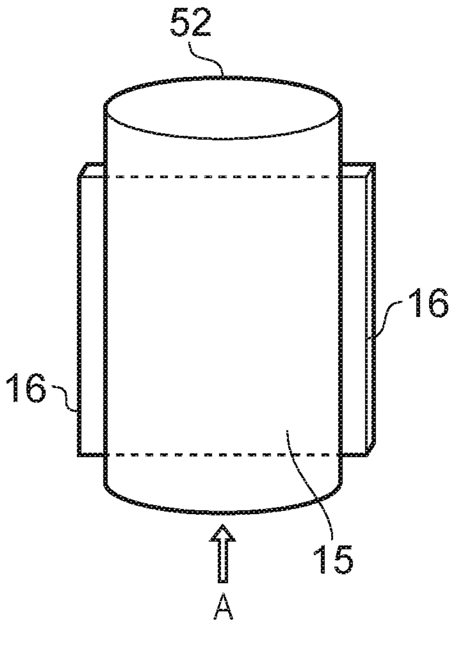
FIG. 7 shows a schematic side view of a further example vaporization chamber.

FIG. 7 shows a schematic representation of a vaporization chamber with a parallel mounted vaporizer; the "edge-on" orientation enables a large wick surface area inside the chamber together with a small profile in the air-flow direction A. The two edges 16 of the wick that are parallel to the air flow direction protrude through the chamber walls for contact with source liquid in a surrounding reservoir.

As another example, the wick may be shaped as a tube and mounted in the vaporization chamber end-on (edge-on) to the air-flow direction so that air flows through it. One or more radial arms can be provided to pass through the chamber walls into the reservoir. Formation of the wick from sintered porous ceramic allows flexibility in wick shape so that more complex forms such as this example can be realized.

Figure 8:
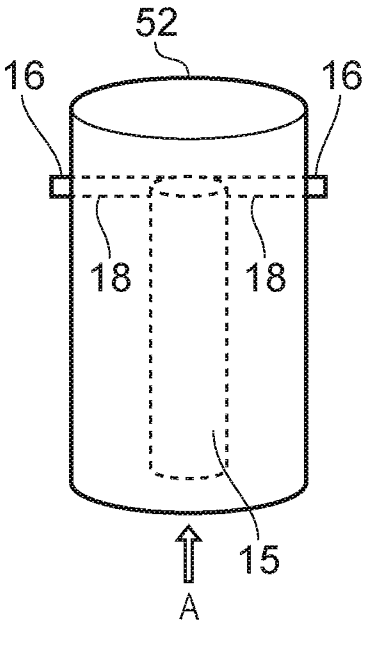
FIG. 8 shows a schematic side view of a yet further example vaporization chamber.

FIG. 8 shows a schematic representation of a vaporization chamber with a tubular vaporizer 15, mounted through apertures in the chamber wall 52 by porous radial arms 18 terminating in end parts 16 that can reach into a surrounding reservoir.

The reservoir need not be configured as an annular space around the vaporization chamber. It may be adjacent to the chamber, rather than around it, so that the reservoir and chamber have a side-by-side or above-and-below configuration. In such a case, likely only one end or edge of the wick would reach into the reservoir, but a curved wick shape could allow more than one edge for this. In any configuration, the reservoir may be immediately adjacent to the vaporization chamber (conveniently they share one or more walls, so that the reservoir and chamber lie on opposite sides of a common wall). This is not essential however, and there may be intervening space between the reservoir and the vaporization chamber that is bridged by part of the wick. Neither the vaporization chamber nor the reservoir need be defined by cylindrical walls; any shape for either volume may be used.

The vaporizer has been described in the context of being included within a cartomizer section of an electronic cigarette. However, the disclosure is not limited in this regard, and the vaporizer may be included otherwise within an electronic cigarette, in a portion which may or may not be intended to be disposable, and may or may not be intended to be separable by the user from another portion or portions of the electronic cigarette. Generally, therefore, the vaporizer is comprised within a sub-assembly of an electronic cigarette, where the sub-assembly may or not be a cartomizer, and may or may not be separable from the remainder of the electronic cigarette.

According to an embodiment a sub-assembly for an electronic vapor provision system, comprises: a reservoir for holding source liquid; a vaporization chamber having an interior in airflow communication with an airflow path through the cartridge assembly; and a vaporizer comprising: a porous wick element with a thickness at least 50 times less than a longest dimension of the wick, such as in the range 50 to 200 times less than a longest dimension of the wick; and a heating element embedded in the wick element and connectable to an electrical power source; wherein the vaporizer is supported in the vaporization chamber by one or more parts of the wick element passing through apertures in a wall of the vaporization chamber, the one or more parts extending into the reservoir such that source liquid in the reservoir is transported by wicking through the wick element to the heating element.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in future.

The invention claimed is:

1. A sub-assembly for an electronic vapor provision system comprising:
 a source of liquid for vaporization; and
 a vaporizer for vaporizing a portion of the liquid for inhalation by a user, the vaporizer comprising:
  a wick component, and
  an electrical heating element comprising a metallic wire embedded in the wick component so that at each cross-sectional position along the wire, the material of the wick component is in contact with the wire around its full circumference;
 wherein the wick component is a sheet of a porous electrically-insulating material and is arranged to wick liquid from the source of liquid to a surface of the wick component adjacent to the embedded electrical heating element for vaporization.

2. The sub-assembly according to claim 1, in which the porous electrically-insulating material is a porous ceramic.

3. The sub-assembly according to claim 1, wherein the wick component has a porosity in a range of 30% to 85%.

4. The sub-assembly according to claim 1, wherein the wick component has a thickness at least 50 times less than a longest dimension of the wick component.

5. The sub-assembly according to claim 1, wherein the heating element has an embedded shape including one or more bends and a length embedded in the wick component of between 2 and 20 times the longest dimension of the wick component.

6. The sub-assembly according to claim 5, wherein the one or more bends define adjacent portions of the heating element that have a center-to-center spacing not greater than twice an embedded width of the heating element.

7. The sub-assembly according to claim 1, wherein a thickness of the wick component is in a range of 105% to 250% of an embedded width of the heating element.

8. The sub-assembly according to claim 1, wherein the heating element is embedded centrally with respect to a thickness of the wick component.

9. The sub-assembly according to claim 1, wherein the wick component is planar.

10. The sub-assembly according to claim 1, wherein the vaporizer is supported in a vaporization chamber by one or more parts of the wick component passing through apertures in one or more walls of the vaporization chamber to extend into the source of liquid.

11. The sub-assembly according to claim 10, wherein the one or more parts of the wick component that pass through apertures in one or more walls of the vaporization chamber are at opposite sides of the wick component.

12. The sub-assembly according to claim 11, wherein the vaporizer is supported in the vaporization chamber such that a thinnest profile of the wick component is presented to a direction of airflow through the vaporization chamber.

13. The sub-assembly according to claim 10, wherein the source of liquid comprises a reservoir having an annular shape and surrounding the vaporization chamber.

14. The sub-assembly according to claim 13, wherein the wall of the vaporization chamber is also an inner wall of the reservoir.

15. The sub-assembly according to claim 1, wherein the sub-assembly is a cartomizer for an electronic vapor provision system.

16. An electronic vapor provision system comprising a sub-assembly according to claim 1.

17. A method of making a vaporizer for an electronic vapor provision system, the method comprising:
 forming an electrically conductive heating element from a metallic wire;
 arranging powdered ceramic material around the heating element in a desired shape for a wick component; and
 sintering the ceramic material to form a porous ceramic wick component with the heating element embedded therein such that at each cross-sectional position along the wire the material of the wick component is in contact with the wire around its full circumference.

18. A method of making a vaporizer for an electronic vapor provision system, the method comprising:
 forming an electrically conductive heating element from a metallic wire;
 arranging the heating element between a first layer and a second layer of sheet porous electrically-insulating material; and
 bonding the first layer and the second layer together to form a porous wick component with the heating element embedded therein such that at each cross-sectional position along the wire, the material of the wick component is in contact with the wire around its full circumference.

19. An electronic vapor provision device comprising:
 a reservoir for source liquid; and a vaporization chamber adjacent the reservoir in which source liquid can be vaporized, the vaporization chamber housing a vaporizer comprising:

a porous ceramic wick component, and a metallic heating element comprising a metallic wire embedded in the wick component such that at each cross-sectional position along the wire, the material of the wick component is in contact with the wire around its full circumference, and connectable to a battery in the electronic vapor provision device;

wherein two ends of the wick component pass through apertures in walls of the vaporization chamber to suspend the vaporizer across the vaporization chamber, the two ends penetrating into the reservoir to absorb source liquid and transport the source liquid to the heating element by capillary action through pores in the wick component.

* * * * *